United States Patent
Macdonald et al.

(10) Patent No.: US 9,951,132 B2
(45) Date of Patent: Apr. 24, 2018

(54) ANTI-PROKINETICIN RECEPTOR (PROKR) ANTIBODIES AND USES THEREOF

(71) Applicant: Regeneron Pharmaceuticals, Inc., Tarrytown, NY (US)

(72) Inventors: Lynn Macdonald, White Plains, NY (US); Michael L. LaCroix-Fralish, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/678,347

(22) Filed: Apr. 3, 2015

(65) Prior Publication Data

US 2015/0266957 A1 Sep. 24, 2015

Related U.S. Application Data

(63) Continuation of application No. 14/078,024, filed on Nov. 12, 2013, now abandoned.

(60) Provisional application No. 61/725,704, filed on Nov. 13, 2012, provisional application No. 61/825,112, filed on May 20, 2013.

(51) Int. Cl.
*A61K 39/395* (2006.01)
*C07K 16/28* (2006.01)
*A61K 39/00* (2006.01)

(52) U.S. Cl.
CPC ........ *C07K 16/28* (2013.01); *A61K 2039/505* (2013.01); *C07K 2317/21* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,891,720 A | 4/1999 | Moore | |
| 6,902,902 B2 | 6/2005 | Unett | |
| 7,045,299 B2 | 5/2006 | Ohtaki | |
| 7,115,560 B2 | 10/2006 | Zhou | |
| 7,297,503 B2 | 11/2007 | Loomis | |
| 7,419,956 B2 | 9/2008 | Ohtaki | |
| 7,615,210 B2 | 11/2009 | Jabbour | |
| 2002/0165380 A1 | 11/2002 | Bard | |
| 2006/0235018 A1 | 10/2006 | Coats | |
| 2012/0035149 A1 | 2/2012 | Zhou | |
| 2014/0130191 A1* | 5/2014 | Pedotti | A01K 67/027 800/9 |

FOREIGN PATENT DOCUMENTS

| | | |
|---|---|---|
| EP | 1302542 | 4/2003 |
| EP | 1386615 | 4/2003 |
| WO | WO 01/36471 | 5/2001 |
| WO | WO 02/06483 | 1/2002 |
| WO | WO 2008/120263 | 10/2008 |
| WO | WO 2008/138536 | 11/2008 |
| WO | WO 2009/042765 | 4/2009 |
| WO | WO 2012/064682 | 5/2012 |

OTHER PUBLICATIONS

Wu, Nie, Huse, and Watkins. Humanization of a murine monoclonal antibody by simultaneous optimization of framework and CDR residues. Journal of Molecular Biology, 1999. vol. 294, pp. 151-162.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Skolnick and Fetrow. From genes to protein structure and function: novel applications of computational approaches in the genomic era. Trends in Biotechnology, 2000. vol. 18, pp. 34-39.*
Bendig, M.M. Humanization of rodent monoclonal antibodies by CDR grafting. Methods: A Companion to Methods in Enzymology, 1995; vol. 8, p. 83-93.*
Paul, W.E. Fundamental Immunology, 3rd Edition, 1993, pp. 292-295.*
MacCallum R.M. et al, Antibody-antigen interactions: Contact analysis and binding site topography. J. Mol. Biol., 1998, vol. 262, p. 732-745.*
Casset F, et al. A peptide mimetic of an anti-CD4 monoclonal antibody by rational design. Biochemical and Biophysical Research Communications, 2003, vol. 307, p. 198-205.*
Tabata, et al. (2013) Oncology Reports 29:459-463, "Endocrine gland-derived vascular endothelial growth factor strengthens cell invasion ability via prokineticin receptor 2 in colon cancer cell lines".
Chen et al., (2005) Molecular Pharmacology 67(6):2070-2076, "Identification and Pharmacological Characterization of Prokineticin 2β as a Selective Ligand for Prokineticin Receptor 1".
Giannini, et al. (2009) PNAS 106(34):14646-14651,"The chemokine Bv8/prokineticin 2 is up-regulated in inflammatory granulocytes and modulates inflammatory pain".
Hu, et al. (2006) Molecular Pain 2(35), "Impaired pain sensation in mice lacking prokineticin 2".
Japanese Patent Application No. H11-241531—English Translation.

(Continued)

*Primary Examiner* — Michael D Pak
(74) *Attorney, Agent, or Firm* — Swanson & Bratschun, L.L.C.

(57) ABSTRACT

The present invention provides antibodies that bind to prokineticin receptors (PROKRs) and methods of using same. According to certain embodiments of the invention, the antibodies are fully human antibodies that bind to human PROKR1 and/or PROKR2. The present invention includes antibodies that bind cell surface-expressed PROKR1 and/or PROKR2. In certain embodiments, the antibodies of the present invention are capable of blocking prokineticin (PK)-mediated activation of one or more PROKR. The antibodies of the invention are useful for the treatment of various diseases and disorders mediated by prokineticin signaling.

14 Claims, 1 Drawing Sheet

(56) References Cited

OTHER PUBLICATIONS

Japanese Patent Application No. 2000-217474—English Translation.
Kimball, et al. (2007) Neurogastroenterol Motil 19:390-400, "Stimulation of neuronal receptors, neuropeptides and cytokines during experimental oil of mustard colitis".
Lin et al. (2002) The Journal of Biological Chemistry 277(22):19276-19280, "Identification and Molecular Characterization of Two Closely Related G Protein-coupled Receptors Activated by Prokineticins/Endocrine Gland Vascular Endothelial Growth Factor".
Maldonado-Perez, et al. (2006) Trends in Endocrinology and Metabolism 18(2):66-72, "Potential roles of prokineticins in reproduction".
Martin, et al. (2011) Endocrine Reviews 32(2):225-246, "The Role of the Prokineticin 2 Pathway in Human Reproduction: Evidence from the Study of Human and Murine Gene Mutations".
Masuda, et al. (2002) Biochemical and Biophysical Research Communications 293:369-402, "Isolation and identification of EG-VEGF/prokineticins as cognate ligands for two orphan G-protein-coupled receptors".
Ngan & Tam (2008) The International Journal of Biochemistry & Cell Biology 40:1679-1684, "Prokineticin-signaling pathway".
Negri, et al. (2006) The Journal of Neuroscience 26(25):6716-6727, "Impaired Nociception and Inflammatory Pain Sensation in Mice Lacking the Prokineticin Receptor PKR1: Focus on Interaction between PKR1and the Capsaicin Receptor TRPV1 in Pain Behavior".
Negri, et al. (2002) British Journal of Pharmacology 137:1147-1154, "Nociceptive sensitization by the secretory protein Bv8".
Negri, et al. (2009) International Review of Neurobiology 85:145-157, "Bv8/Prokineticins and Their Receptors: A New Pronociceptive System".
Parker, et al. (2000) Biochimica et Biophysica Acta 1491:369-375, "Y-receptor-like genes GPR72 and GPR73: molecular cloning, genomic organisation and assignment to human chromosome 11q21.1 and 2p14 and mouse chromosome 9 and 6".
Soga, et al. (2002) Biochimica et Biophysica Acta 1579:173-179, "Molecular cloning and characterization of prokineticin receptors".
U.S. Appl. No. 09/210,279, filed Dec. 10, 1998.
Vellani, et al. (2006) The Journal of Neuroscience 26(19):5109-5116, "Sensitization of Transient Receptor Potential Vanilloid 1 by the Prokineticin Receptor Agonist Bv8".
Brouillet, et al. (2010) Molecular Biology of the Cell 21: 2832-2843, "Molecular Characterization of EG-VEGF-mediated Angiogenesis: Differential Effects on Microvascular and Macrovascular Endothelial Cells".
Brouillet, et al. (2012) Cellular and Molecular Life Science 69:1537-1550, "Revisiting the role of hCGL: new regulation of the angiogenic factor EG-VEGF and its receptors".
LS Bio Catalogue (Nov. 2012) "IHC-plus Antibodies" Retrieved from the Internet: http://www.lsbio.com/cmsdocuments/BookletIHCplusAbs.pdf [retrieved on Jan. 15, 2014].
Negri, et al. (2007) Life Sciences 81:1103-1116, "Bv8/Prokineticin proteins and their receptors".
"PROKR1 Mouse anti-Human Monoclonal Antibody—LS-C66876-LSBio" (Jan. 2012), Retrieved from the Internet: http://www.lsbrio.com/Documents/PDF/Antibodies/67502 [Retrieved on Jan. 9, 2014].
International Search Report and Written Opinion dated Jan. 29, 2014 for International Patent Application No. PCT/US13/69673.
Guilini et al (2010) Am J Physiol Heart Cite Physiol 298:H8449-H852 "Divergent Roles of Prokineticin Receptors in the Endothelial Cells: Angiogenesis and Fenestration".
Negri (2012) Current Opinion in Pharmacology 12:62-66 "Bv8/PK2 and Prokineticin Receptors: a Druggable Pronociceptive System".

* cited by examiner

SEQUENCE LISTING

<160> NUMBER OF SEQ ID NOS: 180

<210> SEQ ID NO 1
<211> LENGTH: 348
<212> TYPE: DNA
<213> ORGANISM: Artificial Sequence
<220> FEATURE:
<223> OTHER INFORMATION: Synthetic

<400> SEQUENCE: 1

```
aacgtgcagc tggtggagtc tggggggaggc ttggttaagc ctggggggtc ccttagactc      60
tcctgtgtag cctccggatt cactttcgct aacgcctgga tgacctgggt ccgccaggct     120
ccagggaagg gtctggagtg ggttggccgt attaaaagta aaactgatgg tgggacaacg     180
gaccacgctg cccccgtgaa aggcagattc atcgtctcaa gagatgattc aaaaagcacg     240
ctgtatctgc aaatgaacag cctgaaaacc gaggacacag ccgtatatta ttgtaccaat     300
tatgcttttc aactctgggg ccaggggaca ttggtcaccg tctcttca                  348
```

<210> SEQ ID NO 2
<211> LENGTH: 116
<212> TYPE: PRT
<213> ORGANISM: Artificial Sequence
<220> FEATURE:
<223> OTHER INFORMATION: Synthetic

<400> SEQUENCE: 2

```
Asn Val Gln Leu Val Glu Ser Gly Gly Gly Leu Val Lys Pro Gly Gly
 1               5                  10                  15

Ser Leu Arg Leu Ser Cys Val Ala Ser Gly Phe Thr Phe Ala Asn Ala
            20                  25                  30

Trp Met Thr Trp Val Arg Gln Ala Pro Gly Lys Gly Leu Glu Trp Val
        35                  40                  45

Gly Arg Ile Lys Ser Lys Thr Asp Gly Gly Thr Thr Asp His Ala Ala
    50                  55                  60

Pro Val Lys Gly Arg Phe Ile Val Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Thr Asn Tyr Ala Phe Gln Leu Trp Gly Gln Gly Thr Leu Val
            100                 105                 110
```

Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcactt tcgctaacgc ctgg                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ala Asn Ala Trp
 1               5

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
attaaaagta aaactgatgg tgggacaacg                                    30

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Ile Lys Ser Lys Thr Asp Gly Gly Thr Thr
 1               5                   10

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
accaattatg cttttcaact c                                             21

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Thr Asn Tyr Ala Phe Gln Leu
 1               5

<210> SEQ ID NO 9
<211> LENGTH: 336
<212> TYPE: DNA
<213> ORGANISM: Artificial Sequence
<220> FEATURE:
<223> OTHER INFORMATION: Synthetic

<400> SEQUENCE: 9

```
gatattgtga tgacccagac tccactctcc tcacttgtca cccttggaca gtcggcctcc      60
atctcctgca ggtctagtca aggcctcgta cacagtgatg gaaacaccta tttgagttgg     120
cttcaccaga ggccaggcca gcctccaaga ctcctaattt ataagatttc taaccggttc     180
tctggggtcc cagacagatt cactggcagt ggggcaggga cagatttcac actgaaaatc     240
agcagggtgg aagctgagga tgtcggggtt tattactgca tgcaatctac acaatttcct     300
cggacgttcg gccaagggac caaggtggaa atcaaa                                336
```

<210> SEQ ID NO 10
<211> LENGTH: 112
<212> TYPE: PRT
<213> ORGANISM: Artificial Sequence
<220> FEATURE:
<223> OTHER INFORMATION: Synthetic

<400> SEQUENCE: 10

```
Asp Ile Val Met Thr Gln Thr Pro Leu Ser Ser Leu Val Thr Leu Gly
 1               5                  10                  15

Gln Ser Ala Ser Ile Ser Cys Arg Ser Ser Gln Gly Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Thr Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Thr Gln Phe Pro Arg Thr Phe Gly Gln Gly Thr Lys Val Glu Ile Lys
               100                 105                 110
```

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11

```
caaggcctcg tacacagtga tggaaacacc tat                                    33
```

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

```
Gln Gly Leu Val His Ser Asp Gly Asn Thr Tyr
 1               5                  10
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 aagatttct                                                                 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Lys Ile Ser
 1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
atgcaatcta cacaatttcc tcggacg                                            27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Met Gln Ser Thr Gln Phe Pro Arg Thr
 1               5

<210> SEQ ID NO 17
<211> LENGTH: 348
<212> TYPE: DNA
<213> ORGANISM: Artificial Sequence
<220> FEATURE:
<223> OTHER INFORMATION: Synthetic

<400> SEQUENCE: 17
gaggtgcagg tggtggagtc tgggggaggc ttggtaaagc ctgggggtc ccttagactc          60 tcctgtgcag cctctggatt cactttcagt aacgtctgga tgacctgggt ccgccaggct        120
ccagggaagg gactggagtg ggttggccgt attaaaagca aaattgaagg tgggacaaca        180
gactacgctg catccgtgaa aggcagattc accatctcaa gagatgactc aaaaaacacg        240
cagtccctgc aaatgaacag cctgaaaagc gaggacacag ccgtttatta ctgttccaca        300
ggtcacttag cttactgggg ccagggaacc ctggtcatcg tctcctca                    348

<210> SEQ ID NO 18
<211> LENGTH: 116
<212> TYPE: PRT
<213> ORGANISM: Artificial Sequence
<220> FEATURE:
<223> OTHER INFORMATION: Synthetic -continued

<400> SEQUENCE: 18

Glu Val Gln Val Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Val
            20                  25                  30

Trp Met Thr Trp Val Arg Gln Ala Pro Gly Lys Gly Leu Glu Trp Val
        35                  40                  45

Gly Arg Ile Lys Ser Lys Ile Glu Gly Gly Thr Thr Asp Tyr Ala Ala
50                  55                  60

Ser Val Lys Gly Arg Phe Thr Ile Ser Arg Asp Asp Ser Lys Asn Thr
65                  70                  75                  80

Gln Ser Leu Gln Met Asn Ser Leu Lys Ser Glu Asp Thr Ala Val Tyr
                85                  90                  95

Tyr Cys Ser Thr Gly His Leu Ala Tyr Trp Gly Gln Gly Thr Leu Val
            100                 105                 110

Ile Val Ser Ser
        115

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcactt tcagtaacgt ctgg                                      24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Asn Val Trp
1               5

<210> SEQ ID NO 21
<211> LENGTH: 30
<212> TYPE: DNA
<213> ORGANISM: Artificial Sequence
<220> FEATURE:
<223> OTHER INFORMATION: Synthetic

<400> SEQUENCE: 21
attaaaagca aaattgaagg tgggacaaca                                30

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Ile Lys Ser Lys Ile Glu Gly Gly Thr Thr
1               5                   10

<210> SEQ ID NO 23
<211> LENGTH: 21

<212> TYPE: DNA
<213> ORGANISM: Artificial Sequence
<220> FEATURE:
<223> OTHER INFORMATION: Synthetic

<400> SEQUENCE: 23
tccacaggtc acttagctta c                                              21

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Ser Thr Gly His Leu Ala Tyr
 1               5

<210> SEQ ID NO 25
<211> LENGTH: 333
<212> TYPE: DNA
<213> ORGANISM: Artificial Sequence
<220> FEATURE:
<223> OTHER INFORMATION: Synthetic

<400> SEQUENCE: 25
gatattgtga tgacccagac tccactctcc tcacctgtct cccttggaca gccggcctcc     60
atctcctgca ggtctagtca aagcctcgta cacagtgatg gaagcaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcgggatt tattactgca tgcaagctac acaatttccg    300
acgttcggcc aagggaccaa ggtggaaatc aaa                                 333

<210> SEQ ID NO 26
<211> LENGTH: 111
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Thr Pro Leu Ser Ser Pro Val Ser Leu Gly
 1               5                  10                  15

Gln Pro Ala Ser Ile Ser Cys Arg Ser Ser Gln Ser Leu Val His Ser
            20                  25                  30

Asp Gly Ser Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
 65                 70                  75                  80

Ser Arg Val Glu Ala Glu Asp Val Gly Ile Tyr Tyr Cys Met Gln Ala
                85                  90                  95

Thr Gln Phe Pro Thr Phe Gly Gln Gly Thr Lys Val Glu Ile Lys
            100                 105                 110

<210> SEQ ID NO 27
<211> LENGTH: 33
<212> TYPE: DNA

<213> ORGANISM: Artificial Sequence
<220> FEATURE:
<223> OTHER INFORMATION: Synthetic

<400> SEQUENCE: 27
caaagcctcg tacacagtga tggaagcacc tac                33

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Gln Ser Leu Val His Ser Asp Gly Ser Thr Tyr
 1               5                   10

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 aagatttct                9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Lys Ile Ser
 1

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
atgcaagcta cacaatttcc gacg                24

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Met Gln Ala Thr Gln Phe Pro Thr
 1               5

<210> SEQ ID NO 33
<211> LENGTH: 348
<212> TYPE: DNA
<213> ORGANISM: Artificial Sequence
<220> FEATURE:
<223> OTHER INFORMATION: Synthetic

<400> SEQUENCE: 33

```
gaggtgcagc tggtggagtc gggggaggc ttggtaaagc ctgggggtc ccttagactc      60
tcctgtgcag cctctggatt cactttcagt aacgcctgga tgagttgggt ccgccaggtt    120
ccagggaagg gctggagtg ggttggccgt attaaaagta aaactgatgg tgggacaaca     180
gactacgctg cacccgtgaa aggcagattc accatctcaa gagatgatcc aaaaaacacg   240
ctgtatctgc aaatgtacag cctgaaaacc gaggacacag ccgtgtatta ctgtaccact   300
cgaagtatgc agtactgggg ccagggaacc ctggtcaccg tctcctca                348
```

<210> SEQ ID NO 34
<211> LENGTH: 116
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Val Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Pro Lys Asn Thr
65                  70                  75                  80

Leu Tyr Leu Gln Met Tyr Ser Leu Lys Thr Glu Asp Thr Ala Val Tyr
                85                  90                  95

Tyr Cys Thr Thr Arg Ser Met Gln Tyr Trp Gly Gln Gly Thr Leu Val
            100                 105                 110

Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcactt tcagtaacgc ctgg                                           24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Asn Ala Trp
1               5

<210> SEQ ID NO 37
<211> LENGTH: 30
<212> TYPE: DNA
<213> ORGANISM: Artificial Sequence
<220> FEATURE:

<223> OTHER INFORMATION: Synthetic

<400> SEQUENCE: 37
attaaaagta aaactgatgg tgggacaaca                                              30

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Ile Lys Ser Lys Thr Asp Gly Gly Thr Thr
 1               5                  10

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
accactcgaa gtatgcagta c                                                      21

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Thr Thr Arg Ser Met Gln Tyr
 1               5

<210> SEQ ID NO 41
<211> LENGTH: 333
<212> TYPE: DNA
<213> ORGANISM: Artificial Sequence
<220> FEATURE:
<223> OTHER INFORMATION: Synthetic

<400> SEQUENCE: 41
gatattgtga tgacccagac tccactctcc tcacctgtca cccttggaca gccggcctcc            60
atctcctgca ggtctagtca aagcctcgta cacagtgatg gatacaccta cttgaattgg           120
cttcagcaga ggccaggcca gcctccaaga ctcctaattt ataagatttc taaccggttc           180
tctggggtcc cagacagatt cagtggcagt ggggcaggga cagatttcac actgaaaatc           240
agcagggtgg aagctgagga tgtcggcatt tattactgca tgcaggctac acaatttccg           300
acgttcggcc aagggaccaa ggtggaaatc aaa                                         333

<210> SEQ ID NO 42
<211> LENGTH: 111
<212> TYPE: PRT
<213> ORGANISM: Artificial Sequence
<220> FEATURE:
<223> OTHER INFORMATION: Synthetic

<400> SEQUENCE: 42

Asp Ile Val Met Thr Gln Thr Pro Leu Ser Ser Pro Val Thr Leu Gly
 1               5                  10                  15

```
Gln Pro Ala Ser Ile Ser Cys Arg Ser Ser Gln Ser Leu Val His Ser
             20                  25                  30

Asp Gly Tyr Thr Tyr Leu Asn Trp Leu Gln Gln Arg Pro Gly Gln Pro
         35                  40                  45

Pro Arg Leu Leu Ile Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Ile Tyr Tyr Cys Met Gln Ala
                 85                  90                  95

Thr Gln Phe Pro Thr Phe Gly Gln Gly Thr Lys Val Glu Ile Lys
            100                 105                 110
```

<210> SEQ ID NO 43
<211> LENGTH: 33
<212> TYPE: DNA
<213> ORGANISM: Artificial Sequence
<220> FEATURE:
<223> OTHER INFORMATION: Synthetic

<400> SEQUENCE: 43
caaagcctcg tacacagtga tggatacacc tac                                    33

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

```
Gln Ser Leu Val His Ser Asp Gly Tyr Thr Tyr
 1               5                  10
```

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 aagatttct                                                                9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Lys Ile Ser
 1

<210> SEQ ID NO 47
<211> LENGTH: 24
<212> TYPE: DNA
<213> ORGANISM: Artificial Sequence
<220> FEATURE:
<223> OTHER INFORMATION: Synthetic

<400> SEQUENCE: 47
atgcaggcta cacaatttcc gacg                                              24

<210> SEQ ID NO 48
<211> LENGTH: 8
<212> TYPE: PRT
<213> ORGANISM: Artificial Sequence
<220> FEATURE:
<223> OTHER INFORMATION: Synthetic

<400> SEQUENCE: 48

Met Gln Ala Thr Gln Phe Pro Thr
1               5

<210> SEQ ID NO 49
<211> LENGTH: 354
<212> TYPE: DNA
<213> ORGANISM: Artificial Sequence
<220> FEATURE:
<223> OTHER INFORMATION: Synthetic

<400> SEQUENCE: 49
gaggtgcagc tggtggagtc tgggggaggc ttggtaaagc ctgggggtc ccttagactc      60 tcctgtgcag cctctggatt cactttcagt aacgcctgga tgacctgggt ccgccaggct    120
ccagggaagg ggctggagtg ggttggccgt attaaaagga aaaatgatgg tgggacaata    180
gactacgctg cacccgtgaa aggcagattc accatctcaa gagatgattc aaaaaacacg    240
ctgtatctac aaatgaacag cctgagaacc gaggacacag ccgtgtatta ctgtatcccc    300
agtgggagct actacggcta ctggggccag ggaaccctgg tcaccgtctc ctca          354

<210> SEQ ID NO 50
<211> LENGTH: 118
<212> TYPE: PRT
<213> ORGANISM: Artificial Sequence
<220> FEATURE:
<223> OTHER INFORMATION: Synthetic

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Gly Arg Ile Lys Arg Lys Asn Asp Gly Gly Thr Ile Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Arg Thr Glu Asp Thr Ala Val Tyr
                85                  90                  95

Tyr Cys Ile Pro Ser Gly Ser Tyr Tyr Gly Tyr Trp Gly Gln Gly Thr
            100                 105                 110

Leu Val Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcactt tcagtaacgc ctgg                                                  24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Asn Ala Trp
1               5

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53
attaaaagga aaaatgatgg tgggacaata                                            30

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

Ile Lys Arg Lys Asn Asp Gly Gly Thr Ile
1               5                   10

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
atccccagtg ggagctacta cggctac                                               27

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Ile Pro Ser Gly Ser Tyr Tyr Gly Tyr
1               5

<210> SEQ ID NO 57
<211> LENGTH: 333
<212> TYPE: DNA
<213> ORGANISM: Artificial Sequence
<220> FEATURE:
<223> OTHER INFORMATION: Synthetic

<400> SEQUENCE: 57
gatattgtga tgacccagac tccactctcc tcacctgtca cccttggaca gccggcctcc     60
atctcctgca ggtctagtca aagcctcgta cacagtgatg gaaacaccta cttgaattgg    120

```
cttcagcaga ggccaggcca gcctccaaga ctcctaattt ataagatttc taaccggttt    180
tctggggtcc cagacagatt cagtggcagt ggggcaggga cagatttcac actgaaaatc    240
agcagggtgg aagctgagga tgtcggggtt tattactgca tgcaaactac acaatttccc    300
acttttggcc aggggaccaa gctggagatc aaa                                 333
```

```
<210> SEQ ID NO 58
<211> LENGTH: 111
<212> TYPE: PRT
<213> ORGANISM: Artificial Sequence
<220> FEATURE:
<223> OTHER INFORMATION: Synthetic

<400> SEQUENCE: 58
```

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr Gln Phe Pro Thr Phe Gly Gln Gly Thr Lys Leu Glu Ile Lys
            100                 105                 110

```
<210> SEQ ID NO 59
<211> LENGTH: 33
<212> TYPE: DNA
<213> ORGANISM: Artificial Sequence
<220> FEATURE:
<223> OTHER INFORMATION: Synthetic

<400> SEQUENCE: 59
caaagcctcg tacacagtga tggaaacacc tac                                  33

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60
```

Gln Ser Leu Val His Ser Asp Gly Asn Thr Tyr
1               5                   10

```
<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 aagatttct                                                             9

<210> SEQ ID NO 62
```

<211> LENGTH: 3
<212> TYPE: PRT
<213> ORGANISM: Artificial Sequence
<220> FEATURE:
<223> OTHER INFORMATION: Synthetic

<400> SEQUENCE: 62

Lys Ile Ser
1

<210> SEQ ID NO 63
<211> LENGTH: 24
<212> TYPE: DNA
<213> ORGANISM: Artificial Sequence
<220> FEATURE:
<223> OTHER INFORMATION: Synthetic

<400> SEQUENCE: 63
atgcaaacta cacaatttcc cact                                          24

<210> SEQ ID NO 64
<211> LENGTH: 8
<212> TYPE: PRT
<213> ORGANISM: Artificial Sequence
<220> FEATURE:
<223> OTHER INFORMATION: Synthetic

<400> SEQUENCE: 64

Met Gln Thr Thr Gln Phe Pro Thr
1               5

<210> SEQ ID NO 65
<211> LENGTH: 354
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtaaagc ctggggggtc ccttagactc     60
tcctgtgcag cctctggatt cactttcagt aacgcctgga tgagctgggt ccgccaggct    120
ccagggaagg ggctggagtg ggttggccgt attaaaagca gaagtgatgg tgggacaaca    180
gactacgctg cacccgtgaa aggcagattc accatttcga gagatgattc aaaaaatacg    240
ctgtatctgc aaatgaacag cctgaaaacc gaggacacag ccttgtatta ctgttccccc    300
cctgggagtc actacggcta ctggggccag ggaaccctgg tcaccgtctc ctca         354

<210> SEQ ID NO 66
<211> LENGTH: 118
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Arg Ser Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
            85                  90                  95

Tyr Cys Ser Pro Pro Gly Ser His Tyr Gly Tyr Trp Gly Gln Gly Thr
        100                 105                 110

Leu Val Thr Val Ser Ser
        115

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcactt tcagtaacgc ctgg                                         24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Ser Asn Ala Trp
1               5

<210> SEQ ID NO 69
<211> LENGTH: 30
<212> TYPE: DNA
<213> ORGANISM: Artificial Sequence
<220> FEATURE:
<223> OTHER INFORMATION: Synthetic

<400> SEQUENCE: 69
attaaaagca gaagtgatgg tgggacaaca                                   30

<210> SEQ ID NO 70
<211> LENGTH: 10
<212> TYPE: PRT
<213> ORGANISM: Artificial Sequence
<220> FEATURE:
<223> OTHER INFORMATION: Synthetic

<400> SEQUENCE: 70

Ile Lys Ser Arg Ser Asp Gly Gly Thr Thr
1               5                   10

<210> SEQ ID NO 71
<211> LENGTH: 27
<212> TYPE: DNA
<213> ORGANISM: Artificial Sequence
<220> FEATURE:
<223> OTHER INFORMATION: Synthetic

<400> SEQUENCE: 71 tcccccctg ggagtcacta cggctac                                       27

<210> SEQ ID NO 72
<211> LENGTH: 9
<212> TYPE: PRT

<213> ORGANISM: Artificial Sequence
<220> FEATURE:
<223> OTHER INFORMATION: Synthetic

<400> SEQUENCE: 72

Ser Pro Pro Gly Ser His Tyr Gly Tyr
 1               5

<210> SEQ ID NO 73
<211> LENGTH: 333
<212> TYPE: DNA
<213> ORGANISM: Artificial Sequence
<220> FEATURE:
<223> OTHER INFORMATION: Synthetic

<400> SEQUENCE: 73

```
gatattgtga tgacccagac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccc     300
acttttggcc aggggaccaa gctggagatc aaa                                  333
```

<210> SEQ ID NO 74
<211> LENGTH: 111
<212> TYPE: PRT
<213> ORGANISM: Artificial Sequence
<220> FEATURE:
<223> OTHER INFORMATION: Synthetic

<400> SEQUENCE: 74

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Thr Phe Gly Gln Gly Thr Lys Leu Glu Ile Lys
            100                 105                 110

<210> SEQ ID NO 75
<211> LENGTH: 33
<212> TYPE: DNA
<213> ORGANISM: Artificial Sequence
<220> FEATURE:
<223> OTHER INFORMATION: Synthetic

<400> SEQUENCE: 75

```
caaagcctcg tacacagtga tggaaacacc tac                                   33
```

<210> SEQ ID NO 76
<211> LENGTH: 11
<212> TYPE: PRT
<213> ORGANISM: Artificial Sequence -continued

```
<220> FEATURE:
<223> OTHER INFORMATION: Synthetic

<400> SEQUENCE: 76

Gln Ser Leu Val His Ser Asp Gly Asn Thr Tyr
 1               5                  10

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 aagatttct                                                                 9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Lys Ile Ser
 1

<210> SEQ ID NO 79
<211> LENGTH: 24
<212> TYPE: DNA
<213> ORGANISM: Artificial Sequence
<220> FEATURE:
<223> OTHER INFORMATION: Synthetic

<400> SEQUENCE: 79
atgcaagcta cacaatttcc cact                                               24

<210> SEQ ID NO 80
<211> LENGTH: 8
<212> TYPE: PRT
<213> ORGANISM: Artificial Sequence
<220> FEATURE:
<223> OTHER INFORMATION: Synthetic

<400> SEQUENCE: 80

Met Gln Ala Thr Gln Phe Pro Thr
 1               5

<210> SEQ ID NO 81
<211> LENGTH: 354
<212> TYPE: DNA
<213> ORGANISM: Artificial Sequence
<220> FEATURE:
<223> OTHER INFORMATION: Synthetic

<400> SEQUENCE: 81
gaggtgcagc tggtggagtc tgggggaggc ttggtaaagc ctggggggtc ccttagactc         60
tcctgtgcag tctctggatt cactttcagt aacgcctgga tgacctgggt ccgccagact        120
ccagggaagg ggctggagtg ggttggccgt attaaaagga aaaatgaggg tgggacaata        180
gactacgctg cacccgtgaa aggcagattc accatctcaa gagatgattc aaaaaacacc        240
ctgtatctgc aaatgaacag cctgaaaacc gaggacacag ccgtgtatta ctgtaccccc        300
agtgggagct attatggcta ctgggggccag ggaaccctgg tcaccgtctc ctca            354
```

<210> SEQ ID NO 82
<211> LENGTH: 118
<212> TYPE: PRT
<213> ORGANISM: Artificial Sequence
<220> FEATURE:
<223> OTHER INFORMATION: Synthetic

<400> SEQUENCE: 82

Glu Val Gln Leu Val Glu Ser Gly Gly Gly Leu Val Lys Pro Gly Gly
1               5                   10                  15

Ser Leu Arg Leu Ser Cys Ala Val Ser Gly Phe Thr Phe Ser Asn Ala
            20                  25                  30

Trp Met Thr Trp Val Arg Gln Thr Pro Gly Lys Gly Leu Glu Trp Val
        35                  40                  45

Gly Arg Ile Lys Arg Lys Asn Glu Gly Gly Thr Ile Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Pro Ser Gly Ser Tyr Tyr Gly Tyr Trp Gly Gln Gly Thr
            100                 105                 110

Leu Val Thr Val Ser Ser
        115

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcactt tcagtaacgc ctgg                                          24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Thr Phe Ser Asn Ala Trp
1               5

<210> SEQ ID NO 85
<211> LENGTH: 30
<212> TYPE: DNA
<213> ORGANISM: Artificial Sequence
<220> FEATURE:
<223> OTHER INFORMATION: Synthetic

<400> SEQUENCE: 85
attaaaagga aaatgagggt gggacaata                                     30

<210> SEQ ID NO 86
<211> LENGTH: 10
<212> TYPE: PRT
<213> ORGANISM: Artificial Sequence
<220> FEATURE:
<223> OTHER INFORMATION: Synthetic

<400> SEQUENCE: 86

Ile Lys Arg Lys Asn Glu Gly Gly Thr Ile
1               5                   10

<210> SEQ ID NO 87
<211> LENGTH: 27
<212> TYPE: DNA
<213> ORGANISM: Artificial Sequence
<220> FEATURE:
<223> OTHER INFORMATION: Synthetic

<400> SEQUENCE: 87 accccagtg ggagctatta tggctac                                    27

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Thr Pro Ser Gly Ser Tyr Tyr Gly Tyr
1               5

<210> SEQ ID NO 89
<211> LENGTH: 333
<212> TYPE: DNA
<213> ORGANISM: Artificial Sequence
<220> FEATURE:
<223> OTHER INFORMATION: Synthetic

<400> SEQUENCE: 89
gatattgtga tgacccagac tccactctcc tcacctgtca cccttggaca gccggcctcc    60
atctcctgca ggtctagtca aagcctcgtg cacagtgatg gaaacaccta cttgagttgg   120
cttcagcaga ggccaggcca gcctccaaga ctcttaattt ataagatttc taaccggttc   180
tctggggtcc cagacagatt cagtggcagt ggggcaggga cagatttcac actgaaaatc   240
agcagggtgg aagctgagga tgtcgggact tattactgca tgcaaactac gcaatttccc   300
acttttggcc aggggaccaa gctggagatc aaa                               333

<210> SEQ ID NO 90
<211> LENGTH: 111
<212> TYPE: PRT
<213> ORGANISM: Artificial Sequence
<220> FEATURE:
<223> OTHER INFORMATION: Synthetic

<400> SEQUENCE: 90

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Thr Tyr Tyr Cys Met Gln Thr

```
                    85                  90                  95
Thr Gln Phe Pro Thr Phe Gly Gln Gly Thr Lys Leu Glu Ile Lys
            100                 105                 110
```

<210> SEQ ID NO 91
<211> LENGTH: 33
<212> TYPE: DNA
<213> ORGANISM: Artificial Sequence
<220> FEATURE:
<223> OTHER INFORMATION: Synthetic

<400> SEQUENCE: 91
caaagcctcg tgcacagtga tggaaacacc tac                             33

<210> SEQ ID NO 92
<211> LENGTH: 11
<212> TYPE: PRT
<213> ORGANISM: Artificial Sequence
<220> FEATURE:
<223> OTHER INFORMATION: Synthetic

<400> SEQUENCE: 92

```
Gln Ser Leu Val His Ser Asp Gly Asn Thr Tyr
 1               5                  10
```

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 aagatttct                                                        9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

```
Lys Ile Ser
 1
```

<210> SEQ ID NO 95
<211> LENGTH: 24
<212> TYPE: DNA
<213> ORGANISM: Artificial Sequence
<220> FEATURE:
<223> OTHER INFORMATION: Synthetic

<400> SEQUENCE: 95
atgcaaacta cgcaatttcc cact                                       24

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

```
Met Gln Thr Thr Gln Phe Pro Thr
 1               5
```

<210> SEQ ID NO 97
<211> LENGTH: 348
<212> TYPE: DNA
<213> ORGANISM: Artificial Sequence
<220> FEATURE:
<223> OTHER INFORMATION: Synthetic

<400> SEQUENCE: 97

```
gaggtgcagc tggtggagtc tgggggaggc ttggtaaagc ctgggggtc ccttagactc      60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gaccacgctg cacccgtgaa aggcagattc accatctcaa gagatgattc aaaaaacacg    240
ctgtatctgc aaatgaacac cttgaaaacc gaggacacag ccgtgtatta ctgtaccaca    300
ggacatagct cctactgggg ccagggaacc ctggtcaccg tctcctca                 348
```

<210> SEQ ID NO 98
<211> LENGTH: 116
<212> TYPE: PRT
<213> ORGANISM: Artificial Sequence
<220> FEATURE:
<223> OTHER INFORMATION: Synthetic

<400> SEQUENCE: 98

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp His Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Thr Leu Lys Thr Glu Asp Thr Ala Val Tyr
                85                  90                  95

Tyr Cys Thr Thr Gly His Ser Ser Tyr Trp Gly Gln Gly Thr Leu Val
            100                 105                 110

Thr Val Ser Ser
        115
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcactt tcagtaacgc ctgg                                            24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

-continued

Gly Phe Thr Phe Ser Asn Ala Trp
1               5

<210> SEQ ID NO 101
<211> LENGTH: 30
<212> TYPE: DNA
<213> ORGANISM: Artificial Sequence
<220> FEATURE:
<223> OTHER INFORMATION: Synthetic

<400> SEQUENCE: 101
attaaaagca aaactgatgg tgggacaaca                                    30

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Ile Lys Ser Lys Thr Asp Gly Gly Thr Thr
1               5                   10

<210> SEQ ID NO 103
<211> LENGTH: 21
<212> TYPE: DNA
<213> ORGANISM: Artificial Sequence
<220> FEATURE:
<223> OTHER INFORMATION: Synthetic

<400> SEQUENCE: 103
accacaggac atagctccta c                                             21

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

Thr Thr Gly His Ser Ser Tyr
1               5

<210> SEQ ID NO 105
<211> LENGTH: 333
<212> TYPE: DNA
<213> ORGANISM: Artificial Sequence
<220> FEATURE:
<223> OTHER INFORMATION: Synthetic

<400> SEQUENCE: 105
gatattgtga tgacccagac tccactctcc tcacctgtca cccttggaca gccggcctcc    60
atctcctgca ggtctagtca aagcctcgta cacagtgatg aaacacccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcggggtt tattactgca tgcaagctac acaatttccc   300
acttttggcc aggggaccaa gctggagatc aaa                                333

<210> SEQ ID NO 106
<211> LENGTH: 111
<212> TYPE: PRT

```
<213> ORGANISM: Artificial Sequence
<220> FEATURE:
<223> OTHER INFORMATION: Synthetic

<400> SEQUENCE: 106

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Thr Phe Gly Gly Gly Thr Lys Leu Glu Ile Lys
            100                 105                 110

<210> SEQ ID NO 107
<211> LENGTH: 33
<212> TYPE: DNA
<213> ORGANISM: Artificial Sequence
<220> FEATURE:
<223> OTHER INFORMATION: Synthetic

<400> SEQUENCE: 107
caaagcctcg tacacagtga tggaaacacc tac                                   33

<210> SEQ ID NO 108
<211> LENGTH: 11
<212> TYPE: PRT
<213> ORGANISM: Artificial Sequence
<220> FEATURE:
<223> OTHER INFORMATION: Synthetic

<400> SEQUENCE: 108

Gln Ser Leu Val His Ser Asp Gly Asn Thr Tyr
1               5                   10

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 aagatttct                                                              9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Lys Ile Ser
1

<210> SEQ ID NO 111
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 111
atgcaagcta cacaatttcc cact                                            24

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

Met Gln Ala Thr Gln Phe Pro Thr
 1               5

<210> SEQ ID NO 113
<211> LENGTH: 348
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttggtaaagc ctggggggtc ccttagactc      60
tcctgtgcag cctctggatt cactttcagt aacgcctgga tgacctgggt ccgccaggct     120
ccagggaagg ggctggagtg ggttggccgt attaaaatca aaactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtaccaca     300
ggacatacct cctactgggg ccagggaacc ctggtcaccg tctcctca                  348

<210> SEQ ID NO 114
<211> LENGTH: 116
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Thr Trp Val Arg Gln Ala Pro Gly Lys Gly Leu Glu Trp Val
         35                  40                  45

Gly Arg Ile Lys Ile Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Gly His Thr Ser Tyr Trp Gly Gln Gly Thr Leu Val
            100                 105                 110

Thr Val Ser Ser
        115
```

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcactt tcagtaacgc ctgg          24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Asn Ala Trp
 1               5

<210> SEQ ID NO 117
<211> LENGTH: 30
<212> TYPE: DNA
<213> ORGANISM: Artificial Sequence
<220> FEATURE:
<223> OTHER INFORMATION: Synthetic

<400> SEQUENCE: 117
attaaaatca aaactgatgg tgggacaaca          30

<210> SEQ ID NO 118
<211> LENGTH: 10
<212> TYPE: PRT
<213> ORGANISM: Artificial Sequence
<220> FEATURE:
<223> OTHER INFORMATION: Synthetic

<400> SEQUENCE: 118

Ile Lys Ile Lys Thr Asp Gly Gly Thr Thr
 1               5                  10

<210> SEQ ID NO 119
<211> LENGTH: 21
<212> TYPE: DNA
<213> ORGANISM: Artificial Sequence
<220> FEATURE:
<223> OTHER INFORMATION: Synthetic

<400> SEQUENCE: 119
accacaggac atacctccta c          21

<210> SEQ ID NO 120
<211> LENGTH: 7
<212> TYPE: PRT
<213> ORGANISM: Artificial Sequence
<220> FEATURE:
<223> OTHER INFORMATION: Synthetic

<400> SEQUENCE: 120

Thr Thr Gly His Thr Ser Tyr
 1               5

<210> SEQ ID NO 121
<211> LENGTH: 333
<212> TYPE: DNA

<213> ORGANISM: Artificial Sequence
<220> FEATURE:
<223> OTHER INFORMATION: Synthetic

<400> SEQUENCE: 121

```
gatattgtga tgacccagac tccactctcc tcacctgtca cccttggaca gccggcctcc    60
atctcctgca ggtctagtca aagcctcgta cacagtgatg gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcggggtt tattactgca tgcaagctac acaatttccc   300
acttttggcc aggggaccaa gctggagatc aaa                                333
```

<210> SEQ ID NO 122
<211> LENGTH: 111
<212> TYPE: PRT
<213> ORGANISM: Artificial Sequence
<220> FEATURE:
<223> OTHER INFORMATION: Synthetic

<400> SEQUENCE: 122

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Thr Phe Gly Gln Gly Thr Lys Leu Glu Ile Lys
            100                 105                 110
```

<210> SEQ ID NO 123
<211> LENGTH: 33
<212> TYPE: DNA
<213> ORGANISM: Artificial Sequence
<220> FEATURE:
<223> OTHER INFORMATION: Synthetic

<400> SEQUENCE: 123

```
caaagcctcg tacacagtga tggaaacacc tac                                 33
```

<210> SEQ ID NO 124
<211> LENGTH: 11
<212> TYPE: PRT
<213> ORGANISM: Artificial Sequence
<220> FEATURE:
<223> OTHER INFORMATION: Synthetic

<400> SEQUENCE: 124

```
Gln Ser Leu Val His Ser Asp Gly Asn Thr Tyr
 1               5                  10
```

<210> SEQ ID NO 125
<211> LENGTH: 9
<212> TYPE: DNA
<213> ORGANISM: Artificial Sequence

```
<220> FEATURE:
<223> OTHER INFORMATION: Synthetic

<400> SEQUENCE: 125 aagatttct                                                                9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Lys Ile Ser
 1

<210> SEQ ID NO 127
<211> LENGTH: 24
<212> TYPE: DNA
<213> ORGANISM: Artificial Sequence
<220> FEATURE:
<223> OTHER INFORMATION: Synthetic

<400> SEQUENCE: 127
atgcaagcta cacaatttcc cact                                              24

<210> SEQ ID NO 128
<211> LENGTH: 8
<212> TYPE: PRT
<213> ORGANISM: Artificial Sequence
<220> FEATURE:
<223> OTHER INFORMATION: Synthetic

<400> SEQUENCE: 128

Met Gln Ala Thr Gln Phe Pro Thr
 1               5

<210> SEQ ID NO 129
<211> LENGTH: 348
<212> TYPE: DNA
<213> ORGANISM: Artificial Sequence
<220> FEATURE:
<223> OTHER INFORMATION: Synthetic

<400> SEQUENCE: 129
gaggtgcagc tggtggagtc tgggggaggc ttggtaaagc ctggggggtc ccttagactc        60
tcctgtgcag cctctggatt cactttcagt aatgtctgga tgacttgggt ccgccaggct       120
ccagggaagg ggctggagtg ggttggccgt attaaaacca aaactgatgg tgggacaaca       180
gactacgctg cacccgtgaa aggcagattc accatctcaa gagatgattc aaaaaactcg       240
ctgtatctgc aaatgagcag cctgaaaacc gaggacacag ccgtgtatta ctgtaccaca       300
ggacatacct cctactgggg ccagggaacc ctggtcaccg tctcctca                    348

<210> SEQ ID NO 130
<211> LENGTH: 116
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Leu Val Lys Pro Gly Gly
 1               5                   10                  15
```

```
Ser Leu Arg Leu Ser Cys Ala Ala Ser Gly Phe Thr Phe Ser Asn Val
         20                  25                  30

Trp Met Thr Trp Val Arg Gln Ala Pro Gly Lys Gly Leu Glu Trp Val
     35                  40                  45

Gly Arg Ile Lys Thr Lys Thr Asp Gly Gly Thr Thr Asp Tyr Ala Ala
 50                  55                  60

Pro Val Lys Gly Arg Phe Thr Ile Ser Arg Asp Asp Ser Lys Asn Ser
65                  70                  75                  80

Leu Tyr Leu Gln Met Ser Ser Leu Lys Thr Glu Asp Thr Ala Val Tyr
                 85                  90                  95

Tyr Cys Thr Thr Gly His Thr Ser Tyr Trp Gly Gln Gly Thr Leu Val
            100                 105                 110

Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcactt tcagtaatgt ctgg                                    24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Phe Ser Asn Val Trp
 1               5

<210> SEQ ID NO 133
<211> LENGTH: 30
<212> TYPE: DNA
<213> ORGANISM: Artificial Sequence
<220> FEATURE:
<223> OTHER INFORMATION: Synthetic

<400> SEQUENCE: 133
attaaaacca aaactgatgg tgggacaaca                              30

<210> SEQ ID NO 134
<211> LENGTH: 10
<212> TYPE: PRT
<213> ORGANISM: Artificial Sequence
<220> FEATURE:
<223> OTHER INFORMATION: Synthetic

<400> SEQUENCE: 134

Ile Lys Thr Lys Thr Asp Gly Gly Thr Thr
 1               5                  10

<210> SEQ ID NO 135
<211> LENGTH: 21
<212> TYPE: DNA
<213> ORGANISM: Artificial Sequence
<220> FEATURE:
<223> OTHER INFORMATION: Synthetic
```

<400> SEQUENCE: 135
accacaggac atacctccta c                                              21

<210> SEQ ID NO 136
<211> LENGTH: 7
<212> TYPE: PRT
<213> ORGANISM: Artificial Sequence
<220> FEATURE:
<223> OTHER INFORMATION: Synthetic

<400> SEQUENCE: 136

Thr Thr Gly His Thr Ser Tyr
 1               5

<210> SEQ ID NO 137
<211> LENGTH: 333
<212> TYPE: DNA
<213> ORGANISM: Artificial Sequence
<220> FEATURE:
<223> OTHER INFORMATION: Synthetic

<400> SEQUENCE: 137
gatattgtga tgacccagac tccactctcc tcacctgtca cccttggaca gccggcctcc     60
atctcctgca ggtctagtca aagcctcgta cacagtgatg gaaacaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcgggggtt tattactgca tgcaagctac acaatttccc    300
acttttggcc aggggaccaa gctggagatc aaa                                 333

<210> SEQ ID NO 138
<211> LENGTH: 111
<212> TYPE: PRT
<213> ORGANISM: Artificial Sequence
<220> FEATURE:
<223> OTHER INFORMATION: Synthetic

<400> SEQUENCE: 138

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Thr Phe Gly Gln Gly Thr Lys Leu Glu Ile Lys
            100                 105                 110

<210> SEQ ID NO 139
<211> LENGTH: 33
<212> TYPE: DNA
<213> ORGANISM: Artificial Sequence
<220> FEATURE:
<223> OTHER INFORMATION: Synthetic

<400> SEQUENCE: 139
caaagcctcg tacacagtga tggaaacacc tac                          33

<210> SEQ ID NO 140
<211> LENGTH: 11
<212> TYPE: PRT
<213> ORGANISM: Artificial Sequence
<220> FEATURE:
<223> OTHER INFORMATION: Synthetic

<400> SEQUENCE: 140

Gln Ser Leu Val His Ser Asp Gly Asn Thr Tyr
 1               5                  10

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 aagatttct                                                      9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Lys Ile Ser
 1

<210> SEQ ID NO 143
<211> LENGTH: 24
<212> TYPE: DNA
<213> ORGANISM: Artificial Sequence
<220> FEATURE:
<223> OTHER INFORMATION: Synthetic

<400> SEQUENCE: 143
atgcaagcta cacaatttcc cact                                    24

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Met Gln Ala Thr Gln Phe Pro Thr
 1               5

<210> SEQ ID NO 145
<211> LENGTH: 348
<212> TYPE: DNA
<213> ORGANISM: Artificial Sequence
<220> FEATURE:
<223> OTHER INFORMATION: Synthetic

<400> SEQUENCE: 145
gaggtgcagc tggtggagtc tgggggaggc ttggtaaagc ctggggggtc ccttagactc    60

```
tcctgtgcag cctctggatt cactttcagt aacgcctgga tgacctgggt ccgccaggct    120
ccagggaagg ggctggagtg ggttggccgt actaaaacca aaactgaagg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccact    300
ggacatattt tttattgggg ccagggaacc ctggtcaccg tctcctca                 348
```

<210> SEQ ID NO 146
<211> LENGTH: 116
<212> TYPE: PRT
<213> ORGANISM: Artificial Sequence
<220> FEATURE:
<223> OTHER INFORMATION: Synthetic

<400> SEQUENCE: 146

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Gly Arg Thr Lys Thr Lys Thr Glu Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly His Ile Phe Tyr Trp Gly Gln Gly Thr Leu Val
            100                 105                 110

Thr Val Ser Ser
        115
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147

```
ggattcactt tcagtaacgc ctgg                                            24
```

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

```
Gly Phe Thr Phe Ser Asn Ala Trp
 1               5
```

<210> SEQ ID NO 149
<211> LENGTH: 30
<212> TYPE: DNA
<213> ORGANISM: Artificial Sequence
<220> FEATURE:
<223> OTHER INFORMATION: Synthetic

<400> SEQUENCE: 149

```
actaaaacca aaactgaagg tgggacaaca                                      30
```

<210> SEQ ID NO 150
<211> LENGTH: 10
<212> TYPE: PRT
<213> ORGANISM: Artificial Sequence
<220> FEATURE:
<223> OTHER INFORMATION: Synthetic

<400> SEQUENCE: 150

```
Thr Lys Thr Lys Thr Glu Gly Gly Thr Thr
1               5                   10
```

<210> SEQ ID NO 151
<211> LENGTH: 21
<212> TYPE: DNA
<213> ORGANISM: Artificial Sequence
<220> FEATURE:
<223> OTHER INFORMATION: Synthetic

<400> SEQUENCE: 151

```
accactggac atatttttta t                                               21
```

<210> SEQ ID NO 152
<211> LENGTH: 7
<212> TYPE: PRT
<213> ORGANISM: Artificial Sequence
<220> FEATURE:
<223> OTHER INFORMATION: Synthetic

<400> SEQUENCE: 152

```
Thr Thr Gly His Ile Phe Tyr
1               5
```

<210> SEQ ID NO 153
<211> LENGTH: 333
<212> TYPE: DNA
<213> ORGANISM: Artificial Sequence
<220> FEATURE:
<223> OTHER INFORMATION: Synthetic

<400> SEQUENCE: 153

```
gatattgtga tgacccagac tccactctcc tcacctgtca cccttggaca gccggcctcc     60
atctcctgca ggtctagtca aagcctcgta cacagtgatg aaacaccta cttgagttgg    120 cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcggggtt tattactgca tgcaagctac acaatttccc   300
acttttggcc aggggaccaa gctggagatc aaa                                333
```

<210> SEQ ID NO 154
<211> LENGTH: 111
<212> TYPE: PRT
<213> ORGANISM: Artificial Sequence
<220> FEATURE:
<223> OTHER INFORMATION: Synthetic

<400> SEQUENCE: 154

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
```

```
            35                  40                  45
Pro Arg Leu Leu Ile Tyr Lys Ile Ser Asn Arg Phe Ser Gly Val Pro
            50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Thr Phe Gly Gln Gly Thr Lys Leu Glu Ile Lys
            100                 105                 110
```

<210> SEQ ID NO 155
<211> LENGTH: 33
<212> TYPE: DNA
<213> ORGANISM: Artificial Sequence
<220> FEATURE:
<223> OTHER INFORMATION: Synthetic

<400> SEQUENCE: 155
caaagcctcg tacacagtga tggaaacacc tac                               33

<210> SEQ ID NO 156
<211> LENGTH: 11
<212> TYPE: PRT
<213> ORGANISM: Artificial Sequence
<220> FEATURE:
<223> OTHER INFORMATION: Synthetic

<400> SEQUENCE: 156

```
Gln Ser Leu Val His Ser Asp Gly Asn Thr Tyr
 1               5                  10
```

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 aagatttct                                                          9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

```
Lys Ile Ser
 1
```

<210> SEQ ID NO 159
<211> LENGTH: 24
<212> TYPE: DNA
<213> ORGANISM: Artificial Sequence
<220> FEATURE:
<223> OTHER INFORMATION: Synthetic

<400> SEQUENCE: 159
atgcaagcta cacaatttcc cact                                         24

<210> SEQ ID NO 160
<211> LENGTH: 8

<212> TYPE: PRT
<213> ORGANISM: Artificial Sequence
<220> FEATURE:
<223> OTHER INFORMATION: Synthetic

<400> SEQUENCE: 160

Met Gln Ala Thr Gln Phe Pro Thr
 1               5

<210> SEQ ID NO 161
<211> LENGTH: 354
<212> TYPE: DNA
<213> ORGANISM: Artificial Sequence
<220> FEATURE:
<223> OTHER INFORMATION: Synthetic

<400> SEQUENCE: 161
gaggtgcagc tggtggagtc tggggggaggc ttgataaagc cggggggggtc ccttagactc    60 tcctgtgcag cctctggatt cactttcagt aacgcctgga tgagctgggt ccgccaggct   120
ccagggaagg ggctggagtg ggttggccgt attaaaagga aaagtgatgg tgggacaaca   180
gactacgctg cacccgtgaa aggcagattc accatttcaa gagatgattc aaaaaacacg   240
atgtatctgc aaatgaacag cctgaaaacc gaggacacag ccgtgtatta ctgtacccc    300 agtgggagct actacggcta ctggggccag ggaaccctgg tcactgtctc ctca         354

<210> SEQ ID NO 162
<211> LENGTH: 118
<212> TYPE: PRT
<213> ORGANISM: Artificial Sequence
<220> FEATURE:
<223> OTHER INFORMATION: Synthetic

<400> SEQUENCE: 162

Glu Val Gln Leu Val Glu Ser Gly Gly Gly Leu Ile Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Arg Lys Ser Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Met Tyr Leu Gln Met Asn Ser Leu Lys Thr Glu Asp Thr Ala Val Tyr
                85                  90                  95

Tyr Cys Thr Pro Ser Gly Ser Tyr Tyr Gly Tyr Trp Gly Gln Gly Thr
            100                 105                 110

Leu Val Thr Val Ser Ser
        115

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcactt tcagtaacgc ctgg                                            24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Ser Asn Ala Trp
1               5

<210> SEQ ID NO 165
<211> LENGTH: 30
<212> TYPE: DNA
<213> ORGANISM: Artificial Sequence
<220> FEATURE:
<223> OTHER INFORMATION: Synthetic

<400> SEQUENCE: 165
attaaaagga aaagtgatgg tgggacaaca                                    30

<210> SEQ ID NO 166
<211> LENGTH: 10
<212> TYPE: PRT
<213> ORGANISM: Artificial Sequence
<220> FEATURE:
<223> OTHER INFORMATION: Synthetic

<400> SEQUENCE: 166

Ile Lys Arg Lys Ser Asp Gly Gly Thr Thr
1               5                   10

<210> SEQ ID NO 167
<211> LENGTH: 27
<212> TYPE: DNA
<213> ORGANISM: Artificial Sequence
<220> FEATURE:
<223> OTHER INFORMATION: Synthetic

<400> SEQUENCE: 167 accccccagtg ggagctacta cggctac                                      27

<210> SEQ ID NO 168
<211> LENGTH: 9
<212> TYPE: PRT
<213> ORGANISM: Artificial Sequence
<220> FEATURE:
<223> OTHER INFORMATION: Synthetic

<400> SEQUENCE: 168

Thr Pro Ser Gly Ser Tyr Tyr Gly Tyr
1               5

<210> SEQ ID NO 169
<211> LENGTH: 333
<212> TYPE: DNA
<213> ORGANISM: Artificial Sequence
<220> FEATURE:
<223> OTHER INFORMATION: Synthetic

<400> SEQUENCE: 169
gatattgtga tgacccagac tccactctcc tcacctgtca cccttggaca gccggcctcc    60
atctcctgca ggtctagtca aagcctcgta cacagtgatg gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240

```
agcagggtgg aagctgagga tgtcggggtt tattactgca tgcaagctac acaatttccc    300
acttttggcc aggggaccaa gctggagatc aaa                                 333
```

<210> SEQ ID NO 170
<211> LENGTH: 111
<212> TYPE: PRT
<213> ORGANISM: Artificial Sequence
<220> FEATURE:
<223> OTHER INFORMATION: Synthetic

<400> SEQUENCE: 170

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Thr Phe Gly Gln Gly Thr Lys Leu Glu Ile Lys
            100                 105                 110
```

<210> SEQ ID NO 171
<211> LENGTH: 33
<212> TYPE: DNA
<213> ORGANISM: Artificial Sequence
<220> FEATURE:
<223> OTHER INFORMATION: Synthetic

<400> SEQUENCE: 171

```
caaagcctcg tacacagtga tggaaacacc tac                                  33
```

<210> SEQ ID NO 172
<211> LENGTH: 11
<212> TYPE: PRT
<213> ORGANISM: Artificial Sequence
<220> FEATURE:
<223> OTHER INFORMATION: Synthetic

<400> SEQUENCE: 172

```
Gln Ser Leu Val His Ser Asp Gly Asn Thr Tyr
 1               5                  10
```

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173

```
aagatttct                                                              9
```

<210> SEQ ID NO 174
<211> LENGTH: 3
<212> TYPE: PRT
<213> ORGANISM: Artificial Sequence
<220> FEATURE:

<223> OTHER INFORMATION: Synthetic

<400> SEQUENCE: 174

Lys Ile Ser
 1

<210> SEQ ID NO 175
<211> LENGTH: 24
<212> TYPE: DNA
<213> ORGANISM: Artificial Sequence
<220> FEATURE:
<223> OTHER INFORMATION: Synthetic

<400> SEQUENCE: 175
atgcaagcta cacaatttcc cact                                         24

<210> SEQ ID NO 176
<211> LENGTH: 8
<212> TYPE: PRT
<213> ORGANISM: Artificial Sequence
<220> FEATURE:
<223> OTHER INFORMATION: Synthetic

<400> SEQUENCE: 176

Met Gln Ala Thr Gln Phe Pro Thr
 1               5

<210> SEQ ID NO 177
<211> LENGTH: 393
<212> TYPE: PRT
<213> ORGANISM: Homo sapiens

<400> SEQUENCE: 177

Met Glu Thr Thr Met Gly Phe Met Asp Asp Asn Ala Thr Asn Thr Ser
 1               5                  10                  15

Thr Ser Phe Leu Ser Val Leu Asn Pro His Gly Ala His Ala Thr Ser
                20                  25                  30

Phe Pro Phe Asn Phe Ser Tyr Ser Asp Tyr Asp Met Pro Leu Asp Glu
            35                  40                  45

Asp Glu Asp Val Thr Asn Ser Arg Thr Phe Phe Ala Ala Lys Ile Val
        50                  55                  60

Ile Gly Met Ala Leu Val Gly Ile Met Leu Val Cys Gly Ile Gly Asn
 65                  70                  75                  80

Phe Ile Phe Ile Ala Ala Leu Val Arg Tyr Lys Lys Leu Arg Asn Leu
                85                  90                  95

Thr Asn Leu Leu Ile Ala Asn Leu Ala Ile Ser Asp Phe Leu Val Ala
            100                 105                 110

Ile Val Cys Cys Pro Phe Glu Met Asp Tyr Tyr Val Val Arg Gln Leu
        115                 120                 125

Ser Trp Glu His Gly His Val Leu Cys Thr Ser Val Asn Tyr Leu Arg
    130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                165                 170                 175

Gln Thr Ala Thr Gly Leu Ile Ala Leu Val Trp Thr Val Ser Ile Leu
            180                 185                 190

Ile Ala Ile Pro Ser Ala Tyr Phe Thr Thr Glu Thr Val Leu Val Ile
        195                 200                 205

```
Val Lys Ser Gln Glu Lys Ile Phe Cys Gly Gln Ile Trp Pro Val Asp
    210                 215                 220
Gln Gln Leu Tyr Tyr Lys Ser Tyr Phe Leu Phe Ile Phe Gly Ile Glu
225                 230                 235                 240
Phe Val Gly Pro Val Val Thr Met Thr Leu Cys Tyr Ala Arg Ile Ser
                245                 250                 255
Arg Glu Leu Trp Phe Lys Ala Val Pro Gly Phe Gln Thr Glu Gln Ile
            260                 265                 270
Arg Lys Arg Leu Arg Cys Arg Lys Thr Val Leu Val Leu Met Cys
        275                 280                 285
Ile Leu Thr Ala Tyr Val Leu Cys Trp Ala Pro Phe Tyr Gly Phe Thr
    290                 295                 300
Ile Val Arg Asp Phe Phe Pro Thr Val Phe Val Lys Glu Lys His Tyr
305                 310                 315                 320
Leu Thr Ala Phe Tyr Ile Val Glu Cys Ile Ala Met Ser Asn Ser Met
                325                 330                 335
Ile Asn Thr Leu Cys Phe Val Thr Val Lys Asn Asp Thr Val Lys Tyr
            340                 345                 350
Phe Lys Lys Ile Met Leu Leu His Trp Lys Ala Ser Tyr Asn Gly Gly
        355                 360                 365
Lys Ser Ser Ala Asp Leu Asp Leu Lys Thr Ile Gly Met Pro Ala Thr
    370                 375                 380
Glu Glu Val Asp Cys Ile Arg Leu Lys
385                 390

<210> SEQ ID NO 178
<211> LENGTH: 384
<212> TYPE: PRT
<213> ORGANISM: Homo sapiens

<400> SEQUENCE: 178

Met Ala Ala Gln Asn Gly Asn Thr Ser Phe Thr Pro Asn Phe Asn Pro
1               5                   10                  15
Pro Gln Asp His Ala Ser Ser Leu Ser Phe Asn Phe Ser Tyr Gly Asp
                20                  25                  30
Tyr Asp Leu Pro Met Asp Glu Asp Glu Asp Met Thr Lys Thr Arg Thr
            35                  40                  45
Phe Phe Ala Ala Lys Ile Val Ile Gly Ile Ala Leu Ala Gly Ile Met
        50                  55                  60
Leu Val Cys Gly Ile Gly Asn Phe Val Phe Ile Ala Ala Leu Thr Arg
65                  70                  75                  80
Tyr Lys Lys Leu Arg Asn Leu Thr Asn Leu Leu Ile Ala Asn Leu Ala
                85                  90                  95
Ile Ser Asp Phe Leu Val Ala Ile Cys Cys Pro Phe Glu Met Asp
                100                 105                 110
Tyr Tyr Val Val Arg Gln Leu Ser Trp Glu His Gly His Val Leu Cys
        115                 120                 125
Ala Ser Val Asn Tyr Leu Arg Thr Val Ser Leu Tyr Val Ser Thr Asn
    130                 135                 140
Ala Leu Leu Ala Ile Ala Ile Asp Arg Tyr Leu Ala Ile Val His Pro
145                 150                 155                 160
Leu Lys Pro Arg Met Asn Tyr Gln Thr Ala Ser Phe Leu Ile Ala Leu
                165                 170                 175
Val Trp Met Val Ser Ile Leu Ile Ala Ile Pro Ser Ala Tyr Phe Ala
            180                 185                 190
```

```
Thr Glu Thr Val Leu Phe Ile Val Lys Ser Gln Glu Lys Ile Phe Cys
            195                 200                 205

Gly Gln Ile Trp Pro Val Asp Gln Gln Leu Tyr Tyr Lys Ser Tyr Phe
210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                245                 250                 255

Gly Phe Gln Thr Glu Gln Ile Arg Lys Arg Leu Arg Cys Arg Arg Lys
            260                 265                 270

Thr Val Leu Val Leu Met Cys Ile Leu Thr Ala Tyr Val Leu Cys Trp
        275                 280                 285

Ala Pro Phe Tyr Gly Phe Thr Ile Val Arg Asp Phe Phe Pro Thr Val
290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                325                 330                 335

Lys Asn Asn Thr Met Lys Tyr Phe Lys Lys Met Met Leu Leu His Trp
            340                 345                 350

Arg Pro Ser Gln Arg Gly Ser Lys Ser Ser Ala Asp Leu Asp Leu Arg
        355                 360                 365

Thr Asn Gly Val Pro Thr Thr Glu Glu Val Asp Cys Ile Arg Leu Lys
370                 375                 380

<210> SEQ ID NO 179
<211> LENGTH: 289
<212> TYPE: PRT
<213> ORGANISM: Artificial Sequence
<220> FEATURE:
<223> OTHER INFORMATION: Synthetic

<400> SEQUENCE: 179

Met Glu Thr Thr Met Gly Phe Met Asp Asp Asn Ala Thr Asn Thr Ser
1               5                   10                  15

Thr Ser Phe Leu Ser Val Leu Asn Pro His Gly Ala His Ala Thr Ser
            20                  25                  30

Phe Pro Phe Asn Phe Ser Tyr Ser Asp Tyr Asp Met Pro Leu Asp Glu
        35                  40                  45

Asp Glu Asp Val Thr Asn Ser Arg Thr Phe Phe Ala Ala Lys Asp Lys
50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175
```

```
Thr Ile Ser Lys Ala Lys Gly Gln Pro Arg Glu Pro Gln Val Tyr Thr
            180                 185                 190

Leu Pro Pro Ser Arg Asp Glu Leu Thr Lys Asn Gln Val Ser Leu Thr
            195                 200                 205

Cys Leu Val Lys Gly Phe Tyr Pro Ser Asp Ile Ala Val Glu Trp Glu
210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
                260                 265                 270

Ala Leu His Asn His Tyr Thr Gln Lys Ser Leu Ser Leu Ser Pro Gly
                275                 280                 285

Lys

<210> SEQ ID NO 180
<211> LENGTH: 280
<212> TYPE: PRT
<213> ORGANISM: Artificial Sequence
<220> FEATURE:
<223> OTHER INFORMATION: Synthetic

<400> SEQUENCE: 180

Met Ala Ala Gln Asn Gly Asn Thr Ser Phe Thr Pro Asn Phe Asn Pro
1               5                   10                  15

Pro Gln Asp His Ala Ser Ser Leu Ser Phe Asn Phe Ser Tyr Gly Asp
            20                  25                  30

Tyr Asp Leu Pro Met Asp Glu Asp Glu Asp Met Thr Lys Thr Arg Thr
        35                  40                  45

Phe Phe Ala Ala Lys Asp Lys Thr His Thr Cys Pro Pro Cys Pro Ala
50                  55                  60

Pro Glu Leu Leu Gly Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Asp Val Ser His Glu Asp Pro Glu Val Lys Phe Asn Trp Tyr Val
            100                 105                 110

Asp Gly Val Glu Val His Asn Ala Lys Thr Lys Pro Arg Glu Glu Gln
        115                 120                 125

Tyr Asn Ser Thr Tyr Arg Val Val Ser Val Leu Thr Val Leu His Gln
130                 135                 140

Asp Trp Leu Asn Gly Lys Glu Tyr Lys Cys Lys Val Ser Asn Lys Ala
145                 150                 155                 160

Leu Pro Ala Pro Ile Glu Lys Thr Ile Ser Lys Ala Lys Gly Gln Pro
                165                 170                 175

Arg Glu Pro Gln Val Tyr Thr Leu Pro Pro Ser Arg Asp Glu Leu Thr
            180                 185                 190

Lys Asn Gln Val Ser Leu Thr Cys Leu Val Lys Gly Phe Tyr Pro Ser
        195                 200                 205

Asp Ile Ala Val Glu Trp Glu Ser Asn Gly Gln Pro Glu Asn Asn Tyr
210                 215                 220

Lys Thr Thr Pro Pro Val Leu Asp Ser Asp Gly Ser Phe Phe Leu Tyr
225                 230                 235                 240
```

-continued

```
Ser Lys Leu Thr Val Asp Lys Ser Arg Trp Gln Gln Gly Asn Val Phe
            245             250                 255

Ser Cys Ser Val Met His Glu Ala Leu His Asn His Tyr Thr Gln Lys
            260             265                 270

Ser Leu Ser Leu Ser Pro Gly Lys
        275             280
```

ANTI-PROKINETICIN RECEPTOR (PROKR) ANTIBODIES AND USES THEREOF

CROSS-REFERENCE TO RELATED APPLICATIONS

This application is a continuation of U.S. patent application Ser. No. 14/078,024 filed Nov. 12, 2013, entitled "Anti-Prokineticin Receptor (PROKR) Antibodies and Uses Thereof" which claims the benefit under 35 U.S.C. § 119(e) of U.S. provisional application Ser. Nos. 61/725,704, filed on Nov. 13, 2012 and 61/825,112, filed on May 20, 2013, the disclosures of which are herein incorporated by reference in their entireties.

FIELD OF THE INVENTION

The present invention relates to antibodies, and antigen-binding fragments thereof, which bind to and/or block a prokineticin receptor (PROKR1 and/or PROKR2), and methods of use thereof.

BACKGROUND

Prokineticins (PK1 and PK2) are secreted, multifunctional chemokine-like peptides. Prokineticins exert their biological functions through the interaction with two G-protein coupled receptors (GPCRs) referred to as prokineticin receptor 1 (PROKR1 or PKR1) and prokineticin receptor 2 (PROKR2 or PKR2). PROKR1 and PROKR2 share approximately 87% overall amino acid sequence identity with one another. PK1 and PK2 each interact with PROKR1 and PROKR2. At the cellular level, activation of prokineticin receptors leads to calcium mobilization, stimulation of phosphoinositide turnover and activation of the MAP kinase signaling pathway. At the multicellular level, prokineticins exhibit angiogenic activity and induce cell proliferation and migration. Prokineticins and their receptors are associated with the development of several human cancers and have also been shown to participate in nociception and the transmission of pain. (See, e.g., Monnier and Samson, 2010, *Cancer Letters* 296:144-149; and Negri et al., 2009, *Int. Rev. Neurobiol.* 85:145-157).

The prokineticin signaling system represents a potential target for the treatment and/or prevention of a variety of diseases and disorders. Accordingly, a need exists in the art for novel therapeutic agents which target and modulate one or more components of the prokineticin signaling pathway, such as the prokineticin receptors (PROKR1 and PROKR2).

BRIEF SUMMARY OF THE INVENTION

The present invention provides antibodies that bind prokineticin receptors (PROKRs). The antibodies of the invention are useful, inter alia, for inhibiting PROKR-mediated signal transduction and for treating diseases and disorders caused by or related to PROKR activity or prokineticin signaling. According to certain embodiments, the anti-PROKR antibodies of the present invention may be used to treat or attenuate pain in a subject in need thereof.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, *J. Immunol.* 164:1925-1933).

The present invention provides anti-PROKR antibodies or antigen-binding fragments thereof comprising a heavy chain variable region (HCVR) having an amino acid sequence selected from the group consisting of SEQ ID NO: 2, 18, 34, 50, 66, 82, 98, 114, 130, 146, and 162, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 106, 122, 138, 154, and 170, or a substantially similar sequence thereof having at least 90%, at least 95%, at least 98% or at least 99% sequence identity.

The present invention also provides an antibody or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 146/154, and 162/170.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 152, and 168, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, and 176, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, and 168/176.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 116, 132, 148, and 164, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, and 166, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, and 172, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, and 174, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H1M6386N); 20-22-24-28-30-32 (e.g. H 2M6385N); 36-38-40-44-46-48 (e.g. H4H6663P); 52-54-56-60-62-64 (e.g. H4H6669P); 68-70-72-76-78-80 (e.g. H4H6671P); 84-86-

88-92-94-96 (e.g. H4H6680P); 100-102-104-108-110-112 (e.g. H4H6690P); 116-118-120-124-126-128 (e.g. H4H6696P); 132-134-136-140-142-144 (e.g. H4H6698P); 148-150-152-156-158-160 (e.g., H4H6701P); and 164-166-168-172-174-176 (e.g. H4 H6706P).

In a related embodiment, the invention includes an anti-PROKR antibody or antigen-binding fragment thereof, wherein the antibody or fragment comprises the heavy and light chain CDR domains derived from heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, and 162/170. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody. Once the CDRs of a reference antibody are identified, new antibodies exhibiting identical or substantially similar binding properties as the reference antibody can be easily made using routine methods in the art.

In another aspect, the invention provides nucleic acid molecules encoding anti-PROKR antibodies or antigen-binding fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, and 161, or a substantially identical sequence having at least 90%, at least 95%, at least 98%, or at least 99% homology thereof.

The present invention also provides an antibody or fragment thereof comprising a LCVR encoded by a nucleic acid sequence selected from the group consisting of SEQ ID NO: 9, 25, 41, 57, 73, 89, 105, 121, 137, 153, and 169, or a substantially identical sequence having at least 90%, at least 95%, at least 98%, or at least 99% homology thereof.

The present invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, and 167, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, and 175, or a substantially identical sequence having at least 90%, at least 95%, at least 98%, or at least 99% homology thereof.

The present invention also provides an antibody or fragment thereof which further comprises a HCDR1 domain encoded by a nucleotide sequence selected from the group consisting of SEQ ID NO: 3, 19, 35, 51, 67, 83, 99, 115, 131, 147, and 163, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, and 165, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, and 171, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, and 173, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: 1 and 9 (e.g. H1M6386N), 17 and 25 (e.g. H2M6385N), 33 and 41 (e.g. H4H6663P), 49 and 57 (e.g. H4H6669P), 65 and 73 (e.g. H4H6671P), 81 and 89 (e.g. H4H6680P), 97 and 105 (e.g. H4H6690P), 113 and 121 (e.g. H4H6696P), 129 and 137 (e.g. H4H6698P), 145 and 153 (e.g. H4H6701P), or 161 and 169 (e.g. H4H6706P).

The present invention includes anti-PROKR antibodies having a modified glycosylation pattern. In some applications, modification to remove undesirable glycosylation sites may be useful, or an antibody lacking a fucose moiety present on the oligosaccharide chain.

In another aspect, the invention provides a pharmaceutical composition comprising an anti-PROKR antibody or antigen-binding fragment thereof and a pharmaceutically acceptable carrier. In a related aspect, the invention features a composition comprising a combination of an anti-PROKR antibody and a second therapeutic agent. In one embodiment, the second therapeutic agent is any agent that is advantageously combined with an anti-PROKR antibody. Exemplary agents that may be advantageously combined with an anti-PROKR antibody include, without limitation, other agents that inhibit PROKR activity (including other antibodies or antigen-binding fragments thereof, peptide inhibitors, small molecule antagonists, natural products, etc.) and/or agents which do not directly bind PROKR but nonetheless interfere with, block or attenuate PROKR-mediated activity or signal transduction.

In yet another aspect, the invention provides methods for inhibiting PROKR activity using an anti-PROKR antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of PROKR activity. The anti-PROKR antibodies or antibody fragments of the invention may function to block the interaction of a PROKR with one or more prokineticin.

The present invention also includes the use of an anti-PROKR antibody or antigen binding portion of an antibody of the invention in the manufacture of a medicament for the treatment of a disease or disorder related to or caused by PROKR activity in a patient.

Other embodiments will become apparent from a review of the ensuing detailed description.

DETAILED DESCRIPTION

Figure 1A:
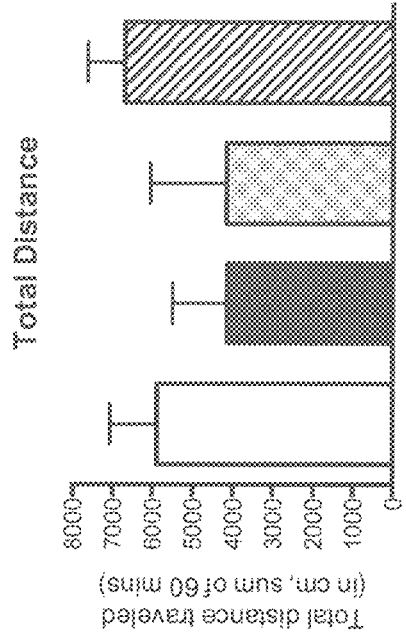
FIG. 1A depicts the extent of immobility time in seconds.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expressions "prokineticin receptor," "PROKR," "PKR," and the like, as used herein, are intended to encompass both PROKR1 and PROKR2. The terms "PROKR1" and "PROKR2" refer to the human PROKR1 or PROKR 2 proteins unless specified as being from a non-human species (e.g., "mouse PROKR1," "mouse PROKR2," "monkey PROKR1," "monkey PROKR2," etc.). Human PROKR1 has the amino acid sequence of SEQ ID NO:177. Human PROKR2 has the amino acid sequence of SEQ ID NO:178. Mouse (Mus musculus) PROKR1 has the amino acid sequence as set forth in NCBI reference sequence number NP_067356.2; mouse PROKR2 has the amino acid sequence as set forth in NCBI reference sequence number NP_659193.3; rat (Rattus norvegicus) PROKR1 has the amino acid sequence as set forth in NCBI reference sequence number NP_620433.1; rat PROKR2 has the amino acid sequence as set forth in NCBI reference sequence number NP_620434.1; cynomolgus monkey (Macaca fascicularis) PROKR1 has the amino acid sequence as set forth in GenBank accession number EHH55625.1; and cynomolgus monkey PROKR2 has the amino acid sequence as set forth in GenBank accession number EHH65528.1.

An "anti-PROKR antibody" means an antibody that specifically binds either PROKR1 or PROKR2, or both PROKR1 and PROKR2. As used herein, "an antibody that binds PROKR" or an "anti-PROKR antibody" includes antibodies, and antigen-binding fragments thereof, that bind a soluble fragment of PROKR protein (e.g., a polypeptide comprising the N-terminal extracellular portion of PROKR1 or PROKR2 [see, e.g., Example 4 herein], or one or more extracellular loops thereof). The expressions "an antibody that binds PROKR" or an "anti-PROKR antibody" also include antibodies that bind cell surface-expressed PROKR1 and/or PROKR2. The expression "cell surface-expressed PROKR" means one or more PROKR protein(s) that is/are expressed on the surface of a cell in vitro or in vivo, such that at least a portion of the PROKR protein (e.g., the N-terminal extracellular portion and/or one or more extracellular loops) is/are exposed to the extracellular side of the cell membrane and accessible to an antigen-binding portion of an antibody. "Cell surface-expressed PROKRs" include PROKRs that are naturally expressed on the surface of a cell as well as PROKRs that are artificially engineered to be expressed on the surface of a cell.

An antibody that "specifically binds cell surface-expressed PROKR1" means an antibody that detectably binds cells that express PROKR1 on the cell surface but does not detectably bind equivalent cells that do not express PROKR1 on the cell surface. Likewise, an antibody that "specifically binds cell surface-expressed PROKR2" means an antibody that detectably binds cells that express PROKR2 on the cell surface but does not detectably bind equivalent cells that do not express PROKR2 on the cell surface. An exemplary method for assessing whether an antibody binds cell surface-expressed PROKR1 and/or PROKR2 is flow cytometry (FACS), as illustrated in Example 3 herein.

The term "antibody", as used herein, means any antigen-binding molecule or molecular complex comprising at least one complementarity determining region (CDR) that specifically binds to or interacts with a particular antigen (e.g., a PROKR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-PROKR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $VL_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

A "neutralizing" or "blocking" antibody, as used herein, is intended to refer to an antibody whose binding to a PROKR: (i) inhibits the interaction between a prokineticin (e.g., PK1 or PK2) and the PROKR; (ii) inhibits or attenuates prokineticin-mediated activation of the PROKR; and/or (iii) results in inhibition of at least one biological function of the PROKR. The inhibition caused by a PROKR-neutralizing or blocking antibody need not be complete so long as it is detectable using an appropriate assay. Exemplary assays for detecting PROKR inhibition are known in the art and are illustrated in the working Examples herein.

The anti-PROKR antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogennicity, etc. Antibodies and antigen-binding fragments obtained in this general manner are encompassed within the present invention.

The present invention also includes anti-PROKR antibodies comprising variants of any of the HCVR, LCVR, and/or CDR amino acid sequences disclosed herein having one or more conservative substitutions. For example, the present invention includes anti-PROKR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24:307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Biological Characteristics of the Antibodies

The present invention includes anti-PROKR antibodies and antigen-binding fragments thereof that specifically bind cell surface-expressed PROKR1 and/or cell surface-expressed PROKR2. For example, the present invention provides anti-PROKR antibodies that: (a) specifically bind cell surface-expressed PROKR1 but not cell surface-expressed PROKR2; (b) specifically bind cell surface-expressed PROKR2 but not cell surface-expressed PROKR1; or (c) specifically bind cell surface-expressed PROKR1 and cell surface-expressed PROKR2. Anti-PROKR antibodies can be tested and evaluated for the ability to specifically bind a cell surface-expressed PROKR using any assay format that allows for the detection of antibody binding to cells that express a PROKR. An exemplary assay format that can be used to determine whether an antibody specifically binds a cell surface-expressed PROKR is illustrated in Example 3 herein. In this Example, cells that normally do not express PROKRs (e.g., HEK293 cells) are engineered to express PROKR1 or PROKR2, and antibody binding to the PROKR-expressing cells is determined by flow cytometry with detectably labeled secondary antibodies. "Specific antibody binding" to a cell surface-expressed PROKR means that the percentage of cells that exhibit detectable binding by flow cytometry is greater than 1%. An antibody that exhibits a binding percentage of between 1% and 10% in this assay format is generally regarded as having "weak" binding, but is nonetheless considered an antibody that "specifically binds a cell surface-expressed PROKR" for purposes of the present disclosure. According to certain embodiments, however, specific antibody binding to a cell surface-expressed PROKR means that the percentage of cells that exhibit detectable binding by flow cytometry is greater than 10%, greater than 20%, greater than 30%, greater than 40%, greater than 50%, or more.

The present invention also includes anti-PROKR antibodies that bind one or more soluble fragments of PROKR1 and/or PROKR2. For example, antibodies are provided herein which specifically bind a soluble fragment of PROKR1 or PROKR2 comprising all or part of the N-terminal extracellular portion of the PROKR protein. Exemplary soluble PROKR1 and PROKR2 constructs of this type are illustrated in Example 4 herein. As shown in Example 4, fusion proteins comprising amino acids 1-62 of PROKR1 (SEQ ID NO:177) or amino acids 1-53 or PROKR2 (SEQ ID NO:178), fused to a human Fc component, were tested for binding to anti-PROKR antibodies by surface plasmon resonance (at 25° C. and pH 7.4). Using an assay format of Example 4, or a similar assay, the binding of anti-PROKR antibodies to soluble PROKR molecules can be quantified, e.g., in terms of equilibrium dissociation constant ($K_D$) and/or dissociation half-life (t½).

Thus, the present invention provides anti-PROKR antibodies that bind soluble human PROKR1 (e.g., N-terminal portion) with a $K_D$ of less than about 5 nM, less than about 3 nM, less than about 2 nM, less than about 1.5 nM, less than about 600 pM, less than about 550 pM, less than about 500 pM, less than about 450 pM, less than about 400 pM, less than about 350 pM, less than about 300 pM, less than about 250 pM, less than about 200 pM, less than about 150 pM, or less than about 100 pM as measured by surface plasmon resonance, e.g., using the assay format as defined in Example 4 herein or a substantially similar assay.

The present invention also includes anti-PROKR antibodies and antigen-binding fragments thereof that bind soluble human PROKR1 (e.g., N-terminal portion) with a dissociation half-life (t½) of greater than about 5 minutes, greater than about 10 minutes, greater than about 15 minutes, greater than about 20 minutes, greater than about 25 minutes, greater than about 30 minutes, greater than about 35 minutes, greater than about 40 minutes, greater than about 45 minutes, greater than about 50 minutes, greater than about 55 minutes, greater than about 60 minutes, greater than about 75 minutes, greater than about 100 minutes, greater than about 150 minutes, greater than about 200 minutes, or greater than about 250 minutes, or more, as measured by surface plasmon resonance, e.g., using the assay format as defined in Example 4 herein or a substantially similar assay.

The present invention also provides anti-PROKR antibodies that bind soluble human PROKR2 (e.g., N-terminal portion) with a $K_D$ of less than about 150 nM, less than about 130 nM, less than about 100 nM, less than about 90 nM, less than about 80 nM, less than about 75 nM, less than about 70 nM, less than about 65 nM, less than about 60 nM, less than about 55 nM, less than about 50 nM, less than about 45 nM, less than about 40 nM, less than about 35 nM, less than about 30 nM, less than about 25 nM, less than about 20 nM, less than about 15 nM, less than about 10 nM, less than about 5 nM, less than about 3 nM, or less, as measured by surface plasmon resonance, e.g., using the assay format as defined in Example 4 herein or a substantially similar assay.

The present invention also includes anti-PROKR antibodies and antigen-binding fragments thereof that bind soluble human PROKR2 (e.g., N-terminal portion) with a dissociation half-life (t½) of greater than about 1 minute, greater than about 2 minutes, greater than about 3 minutes, greater than about 4 minutes, greater than about 5 minutes, greater than about 10 minutes, greater than about 20 minutes, greater than about 30 minutes, greater than about 40 minutes, or more, as measured by surface plasmon resonance, e.g., using the assay format as defined in Example 4 herein or a substantially similar assay.

The present invention also includes anti-PROKR antibodies and antigen-binding fragments thereof that block prokineticin-mediated activation of PROKR1 and/or PROKR2. The ability of anti-PROKR antibodies to block prokineticin-mediated activation of PROKR1 and/or PROKR2 can be measured, e.g., using the assay format illustrated in Example 5 herein. In this assay, cells that do not normally express human PROKRs (i.e., HEK293 cells) are engineered to express PROKR1 or PROKR2. In this assay format, the extent of PROKR activation is indicated by calcium mobilization following treatment with prokineticin-1 (PK1) or prokineticin-2 (PK2) (e.g. using a concentration of about 1 to 20 nM or PK1 or PK2), in the presence or absence of an anti-PROKR antibody. Inhibition of prokineticin-mediated PROKR activation in this assay format is calculated as an $IC_{50}$ value (i.e., the concentration of antibody needed to inhibit PK-mediated calcium flux by 50%) or as a blocking percentage. The present invention includes anti-PROKR antibodies that block: (a) PK1-mediated activation of PROKR1; (b) PK2-mediated activation of PROKR1; (c) PK1-mediated activation of PROKR2; and/or (d) PK2-mediated activation of PROKR2. For example, the present invention includes anti-PROKR antibodies that block PK1-mediated activation of PROKR1 with an $IC_{50}$ of less than about 20 nM, less than about 18 nM, less than about 16 nM, less than about 14 nM, less than about 12 nM, less than about 10 nM, less than about 9 nM, less than about 8 nM, less than about 7 nM, or less than about 6 nM, or less, as measured using the assay format of Example 5 (e.g., using about 1 nM to about 20 nM of PK1), or a substantially similar assay. The present invention also includes anti-PROKR antibodies that block PK2-mediated activation of PROKR1 with an $IC_{50}$ of less than about 60 nM, less than about 50 nM, less than about 20 nM, or less than about 20 nM, as measured using the assay format of Example 5 (e.g., using about 1 nM to about 20 nM of PK2), or a substantially similar assay.

The present invention also includes anti-PROKR antibodies that inhibit or reduce pain response(s) in various animal pain models.

Other biological activities of the anti-PROKR antibodies of the present invention will be apparent to persons of ordinary skill in the art in light of the working Examples set forth herein.

Epitope Mapping and Related Technologies

The present invention includes anti-PROKR antibodies which interact with one or more amino acids located within one or more regions or segments of the PROKR1 molecule selected from the group consisting of: (a) the N-terminal extracellular region (amino acids 1 to 62 of SEQ ID NO:177); (b) extracellular loop 1 (amino acids 120 to 146 of SEQ ID NO: 177); (c) extracellular loop 2 (amino acids 201 to 232 of SEQ ID NO:177); and/or extracellular loop 3 (amino acids 304 to 322 of SEQ ID NO:177).

The present invention also includes anti-PROKR antibodies which interact with one or more amino acids located within one or more regions or segments of the PROKR2 molecule selected from the group consisting of: (a) the N-terminal extracellular region (amino acids 1 to 54 of SEQ ID NO:178); (b) extracellular loop 1 (amino acids 110 to 137 of SEQ ID NO:178); (c) extracellular loop 2 (amino acids 193 to 221 of SEQ ID NO:178); and/or extracellular loop 3 (amino acids 297 to 310 of SEQ ID NO:178).

The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned regions or segments of PROKR1 and/or PROKR2. Alternatively, the epitope may consist of a plurality of non-contiguous amino acids (or amino acid sequences) located within one or more of the aforementioned regions or segments of a PROKR molecule. For example, the antibodies of the present invention may interact with one or more amino acids located within the N-terminal extracellular region of PROKR1 as well as one or more amino acids located within one or more extracellular loops of PROKR1.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

The present invention further includes anti-PROKR antibodies that bind to the same epitope as any of the specific exemplary antibodies described herein (e.g. H1M6386N, H2M6385N, H4H6663P, H4H6669P, H4H6671P, H4H6680P, H4H6690P, H4H6696P, H4H6698P, H4H6701P, H4H6706P, etc.). Likewise, the present invention also includes anti-PROKR antibodies that compete for binding to PROKR1 and/or PROKR2 with any of the specific exemplary antibodies described herein (e.g. H1M6386N, H2M6385N, H4H6663P, H4H6669P, H4H6671P, H4H6680P, H4H6690P, H4H6696P, H4H6698P, H4H6701P, H4H6706P, etc.).

One can easily determine whether an antibody binds to the same epitope as, or competes for binding with, a reference anti-PROKR antibody by using routine methods known in the art. For example, to determine if a test antibody binds to the same epitope as a reference anti-PROKR antibody of the invention, the reference antibody is allowed to bind to a PROKR protein. Next, the ability of a test antibody to bind to the PROKR molecule is assessed. If the test antibody is able to bind to the PROKR following saturation binding with the reference anti-PROKR antibody, it can be concluded that the test antibody binds to a different epitope than the reference anti-PROKR antibody. On the other hand, if the test antibody is not able to bind to the PROKR molecule following saturation binding with the reference anti-PROKR antibody, then the test antibody may bind to the same epitope as the epitope bound by the reference anti-PROKR antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20-or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-PROKR antibody, the above-described binding methodology is performed in two orientations: In a first orientation, the reference antibody is allowed to bind to a PROKR protein under saturating conditions followed by assessment of binding of the test antibody to the PROKR molecule. In a second orientation, the test antibody is allowed to bind to a PROKR molecule under saturating conditions followed by assessment of binding of the reference antibody to the PROKR molecule. If, in both orientations, only the first (saturating) antibody is capable of binding to the PROKR molecule, then it is concluded that the test antibody and the reference antibody compete for binding to the PROKR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to a human PROKR.

Using VELOCIMMUNE™ technology or other similar methods for generating monoclonal antibodies, high affinity chimeric antibodies to PROKR are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-PROKR antibodies and antibody fragments of the present invention encompass proteins having amino acid sequences that vary from those of the described antibodies but that retain the ability to bind a human PROKR. Such variant antibodies and antibody fragments comprise one or more additions, deletions, or substitutions of amino acids when compared to parent sequence, but exhibit biological activity that is essentially equivalent to that of the described antibodies. Likewise, the anti-PROKR antibody-encoding DNA sequences of the present invention encompass sequences that comprise one or more additions, deletions, or substitutions of nucleotides when compared to the disclosed sequence, but that encode an anti-PROKR antibody or antibody fragment that is essentially bioequivalent to an anti-PROKR antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-PROKR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-PROKR antibody variants comprising amino acid changes which modify the glycosylation characteristics of the antibodies, e.g., mutations which eliminate or remove glycosylation.

Species Selectivity and Species Cross-Reactivity

The present invention includes anti-PROKR antibodies that bind to a human PROKR (e.g., cell surface-expressed human PROKR1 and/or cell surface expressed human PROKR2) but not to PROKRs from other species. The present invention also includes anti-PROKR antibodies that bind to a human PROKR (e.g., cell surface-expressed human PROKR1 and/or cell surface expressed human PROKR2) and also bind to one or more PROKR proteins from one or more non-human species. The present invention also includes anti-PROKR antibodies that block prokineticin-mediated activation of human PROKR1 and/or human PROKR2 but do not block prokineticin-mediated activation of one or more non-human PROKRs. The present invention also includes anti-PROKR antibodies that block prokineticin-mediated activation of human PROKR1 and/or human PROKR2 and also block prokineticin-mediated activation of one or more non-human PROKRs.

For example, the anti-PROKR antibodies of the invention may bind to and/or block human PROKR1 and/or human PROKR2, and may bind and/or block (or not bind or not block as the case may be) one or more of mouse, rat, guinea pig, hamster, gerbil, pig, cat, dog, rabbit, goat, sheep, cow, horse, camel, cynomologous, marmoset, rhesus or chimpanzee PROKR1 or PROKR2. For example, as shown in Example 5 herein, certain exemplary antibodies of the present invention block PK1-mediated activation of human PROKR1 as well as PK1-mediated activation of monkey PROKR1 (e.g., H4H6696, H4H6698, H4H6701 and H4H6385). On the other hand, antibody H1M6386 exhibited potent blocking of PK1-mediated activation of human PROKR1 but did not exhibit any detectable blocking of PK1-mediated activation of monkey PROKR1. Other cross-reactivity/cross-blocking patterns of the exemplary anti-PROKR antibodies of the present invention will be apparent to a person of ordinary skill in the art upon review of the working examples provided herein.

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-PROKR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for a human PROKR or a fragment thereof, and the other arm of the immunoglobulin is specific for a second therapeutic target or is conjugated to a therapeutic moiety. The present invention includes bispecific antibodies comprising a first antigen-binding domain that specifically binds PROKR1 and a second antigen-binding domain that specifically binds PROKR2.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Formulation and Administration

The present invention provides pharmaceutical compositions comprising the anti-PROKR antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with PROKR activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-PROKR antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25 ™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an anti-PROKR antibody. The therapeutic composition can comprise any of the anti-PROKR antibodies, or fragments thereof, as disclosed herein. As used herein, the expression "a subject in need thereof" means a human or non-human animal that exhibits one or more symptoms or indicia of a disease or disorder associated with or caused by PROKR activity, or who otherwise would benefit from an inhibition or reduction PROKR signaling.

Exemplary diseases and disorders that can be treated with the anti-PROKR antibodies of the present invention include pain conditions (e.g., acute, chronic, or breakthrough pain). Exemplary types of pain conditions that are treatable with the anti-PROKR antibodies of the present invention include nociceptive pain, visceral pain (e.g., pain from inflammatory bowel disease/irritable bowel syndrome, interstitial cystitis, pancreatitis, endometriosis, chronic pelvic pain syndrome, etc.), as well as pain associated with inflammation (e.g., inflammatory muscle pain), post-operative incision (e.g., post-surgical pain), neuropathy (e.g., diabetic neuropathy), sciatica, post-herpetic neuralgia, myofascial pain syndromes, arthritis, sickle cell, enteric nerve ischemia, claudication pain, bone fracture, burn, osteoporotic fracture, gout, migraine headache, fibromyalgia, complex regional pain syndrome, acute herpetic pain, etc.

The anti-PROKR antibodies of the present invention are also useful for treating or preventing cancer-associated pain. "Cancer-associated pain" includes, e.g., bone cancer pain, including pain from cancer that has metastasized to bone (e.g., breast cancer, prostate cancer, lung cancer, sarcoma, kidney cancer, multiple myeloma, etc.). "Cancer-associated pain" also includes pain more generally associated with cancerous conditions such as, e.g., renal cell carcinoma, pancreatic carcinoma, breast cancer, head and neck cancer, prostate cancer, malignant gliomas, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma.

The antibodies of the present invention may also be useful in treating diseases and disorders associated with and/or caused by pathological angiogenesis (e.g., tumors, angiogenic eye disorders, etc.). Other diseases and disorders that may be treated using the anti-PROKR antibodies of the present invention include, e.g., disorders of the gastrointestinal tract (e.g., involving smooth muscle contraction), Hirschsprung disease, polycystic ovarian syndrome, Kallman syndrome, rheumatoid arthritis, and osteoarthritis. The anti-PROKR antibodies of the present invention may also be used for fertility applications.

Combination Therapies and Formulations

The present invention provides methods which comprise administering a pharmaceutical composition comprising any of the exemplary anti-PROKR antibodies described herein in combination with one or more additional therapeutic agents. Exemplary additional therapeutic agents that may be combined with or administered in combination with an anti-PROKR antibody of the present invention include, e.g., other pain-attenuating biologics such as anti-NGF antibodies, anti-PAR2 antibodies, anti-ASIC antibodies (e.g., anti-ASIC1, anti-ASIC2, anti-ASIC3, and anti-ASIC4 antibodies), anti-GFRα antibodies, as well as non-biologic therapeutic agents such as antivirals, antibiotics, analgesics, corticosteroids, opioids, and/or NSAIDs.

The anti-PROKR antibodies of the present invention may also be combined with or administered in combination with one or more cancer therapeutic agent(s) such as, e.g., an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFRI-β antibody), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a PRLR antagonist (e.g., an anti-PRLR antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin antibody), a CD20 antagonist (e.g., an anti-CD20 antibody such as rituximab), etc.

Other agents that may be beneficially administered in combination with the anti-PROKR antibodies of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or antagonists of their respective receptors, as well as anti-IgE antibodies, anti-TNF antibodies, etc.

The additional therapeutically active component(s) may be administered just prior to, concurrent with, or shortly after the administration of an anti-PROKR antibody of the present invention; (for purposes of the present disclosure, such administration regimens are considered the administration of an anti-PROKR antibody "in combination with" an additional therapeutically active component). The present invention includes pharmaceutical compositions in which an anti-PROKR antibody of the present invention is co-formulated with one or more of the additional therapeutically active component(s) as described elsewhere herein.

Administration Regimens

According to certain embodiments of the present invention, multiple doses of an anti-PROKR antibody may be administered to a subject over a defined time course. The methods according to this aspect of the invention comprise sequentially administering to a subject multiple doses of an anti-PROKR antibody of the invention. As used herein, "sequentially administering" means that each dose of anti-PROKR antibody is administered to the subject at a different point in time, e.g., on different days separated by a predetermined interval (e.g., hours, days, weeks or months). The present invention includes methods which comprise sequentially administering to the patient a single initial dose of an anti-PROKR antibody, followed by one or more secondary doses of the anti-PROKR antibody, and optionally followed by one or more tertiary doses of the anti-PROKR antibody.

The terms "initial dose," "secondary doses," and "tertiary doses," refer to the temporal sequence of administration of the anti-PROKR antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-PROKR antibody, but generally may differ from one another in terms of frequency of administration. In certain embodiments, however, the amount of anti-PROKR antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½21, 21½, 22, 22½, 23, 23½, 24, 24½25, 25½26, 26½, or more) weeks after the immediately preceding dose. The phrase "the immediately preceding dose," as used herein, means, in a sequence of multiple administrations, the dose of anti-PROKR antibody which is administered to a patient prior to the administration of the very next dose in the sequence with no intervening doses.

The methods according to this aspect of the invention may comprise administering to a patient any number of secondary and/or tertiary doses of an anti-PROKR antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-PROKR antibodies of the present invention may also be used to detect and/or measure one or more PROKR protein(s), or PROKR-expressing cells in a sample, e.g., for diagnostic purposes. For example, an anti-PROKR antibody, or fragment thereof, may be used to diagnose a condition or disease characterized by aberrant expression (e.g., over-expression, under-expression, lack of expression, etc.) of PROKR1 or PROKR2. Exemplary diagnostic assays for PROKR may comprise, e.g., contacting a sample, obtained from a patient, with an anti-PROKR antibody of the invention, wherein the anti-PROKR antibody is labeled with a detectable label or reporter molecule. Alternatively, an unlabeled anti-PROKR antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure PROKR in a sample include enzyme-linked immunosorbent assay (ELISA), radioimmunoassay (RIA), and fluorescence-activated cell sorting (FACS).

Samples that can be used in PROKR diagnostic assays according to the present invention include any tissue or fluid sample obtainable from a patient which contains detectable quantities of PROKR protein, or fragments thereof, under normal or pathological conditions. Generally, levels of PROKR in a particular sample obtained from a healthy patient (e.g., a patient not afflicted with a disease or condition associated with abnormal PROKR levels or activity) will be measured to initially establish a baseline, or standard, level of PROKR. This baseline level of PROKR can then be compared against the levels of PROKR measured in samples obtained from individuals suspected of having a PROKR related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Prokineticin Receptors

To generate anti-PROKR antibodies, a VELOCIMMUNE® mouse, comprising DNA encoding human Immunoglobulin heavy and kappa light chain variable regions, was immunized with a mouse fibroblast cell line (MG87) engineered to express either human PROKR1 or human PROKR2. The antibody immune response was monitored by a cell binding assay using cells engineered to express human PROKRs. When a desired immune response was achieved, splenocytes were harvested and fused with mouse myeloma cells to preserve their viability and form hybridoma cell lines. The hybridoma cell lines were screened and selected to identify cell lines that produce PROKR-specific antibodies. Using this technique anti-PROKR chimeric antibodies (i.e., antibodies possessing human variable domains and mouse constant domains) were obtained, including antibodies designated H1M6386N and H2M6385N.

Anti-PROKR antibodies were also isolated directly from antigen-positive B cells without fusion to myeloma cells, as described in US 2007/0280945 A1. Using this method, several fully human anti-PROKR antibodies (i.e., antibodies possessing human variable domains and human constant domains) were obtained; exemplary antibodies generated in this manner were designated as follows: H4H6663P, H4H6669P, H4H6671P, H4H6680P, H4H6690P, H4H6696P, H4H6698P, H4H6701P, and H4H6706P.

Certain biological properties of the exemplary anti-PROKR antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected anti-PROKR antibodies and their corresponding antibody identifiers.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 6386N | 2 | 4 | 6 | 8 | 10 | 12 | 14 | 16 |
| 6385N | 18 | 20 | 22 | 24 | 26 | 28 | 30 | 32 |
| 6663P | 34 | 36 | 38 | 40 | 42 | 44 | 46 | 48 |
| 6669P | 50 | 52 | 54 | 56 | 58 | 60 | 62 | 64 |
| 6671P | 66 | 68 | 70 | 72 | 74 | 76 | 78 | 80 |
| 6680P | 82 | 84 | 86 | 88 | 90 | 92 | 94 | 96 |
| 6690P | 98 | 100 | 102 | 104 | 106 | 108 | 110 | 112 |
| 6696P | 114 | 116 | 118 | 120 | 122 | 124 | 126 | 128 |
| 6698P | 130 | 132 | 134 | 136 | 138 | 140 | 142 | 144 |
| 6701P | 146 | 148 | 150 | 152 | 154 | 156 | 158 | 160 |
| 6706P | 162 | 164 | 166 | 168 | 170 | 172 | 174 | 176 |

Antibodies are typically referred to herein according to the following nomenclature: Fc prefix (e.g. "H1M," "H4H"), followed by a numerical identifier (e.g. "6386," "6385," "6663," etc. as shown in Table 1), followed by a "P" or "N" suffix. Thus, according to this nomenclature, an antibody may be referred to herein as, e.g., "H1M6386N," "H2M6385N," "H4H6663P," etc. The Fc prefixes on the antibody designations used herein indicate the particular Fc region of the antibody. For example, an "H1M" antibody has a mouse IgG1 Fc, whereas an "H4H" antibody has a human IgG4 Fc. As will be appreciated by a person of ordinary skill in the art, an antibody with a particular IgG isotype (e.g., "H4H") can be converted to an antibody with a different IgG isotype (e.g., H1H, H1M, H2M, etc.) using routine methods; but in any event, the variable domains (including the CDRs)—which are indicated by the numerical identifiers shown in Table 1—will remain the same, and the binding properties are expected to be identical or substantially similar regardless of the nature of the Fc domain.

Example 3

Determination of the Binding of Anti-PROKR Antibodies to Cell-Surface PROKR1 and PROKR2 by Flow Cytometry Anti-PROKR antibodies generated in accordance with Example 1 were tested for the ability to bind to human, mouse, and monkey PROKR1 and PROKR2. For these experiments, HEK293 cells were engineered to express: human PROKR1; human PROKR2; mouse PROKR1; mouse PROKR2; cynomolgus monkey PROKR1; or cynomolgus monkey PROKR2. Binding of anti-human PROKR antibodies to the PROKR-expressing cell lines was measured by flow cytometry. The experimental protocol is set forth below, and the results are summarized in Table 2.

Adherent cells were collected using 1 mM EDTA in PBS, then washed, and re-suspended in cold PBS containing 5% FBS. For the binding experiments, each anti-PROKR antibody was added to 250,000 cells in 500 µl of PBS with 5% FBS (final antibody concentration of 13 nM). After incubation for 20 minutes at room temperature, the cells were washed with PBS containing 5% FBS. A secondary antibody, recognizing either human (Jackson Immuno Research, #115-135-205) or mouse Fc (BD Pharmigen, #550826) and conjugated to allophycyanin, was then added to the cell mixture at a final concentration of 13.3 nM. After incubating for 20 minutes on ice, the cells were washed and resuspended in PBS containing 5% FBS and then sorted and analyzed on a FACSCalibur (BD Biosciences) flow cytometer to determine relative binding by the candidate antibodies. The cell samples containing secondary antibody alone were used as negative control for FACS gating. Histograms of cells stained with anti-human PROKR antibodies were compared with cells stained with secondary alone. The percentage of cells exhibiting a PROKR FACS binding signal greater than the signal observed with secondary antibody alone ("percentage binding") was calculated by FlowJo software (Tree Star). The samples stained with anti-PROKR antibodies were recorded as FACS positive ("Pos" in Table 1) when percentage binding was greater than 10%. The samples stained with anti-human PROKR antibodies were recorded as FACS negative ("Neg" in Table 1) when percentage binding was lower than 1% or when signal was detected on parental cells (i.e., background signal). The samples stained with anti-human PROKR antibody were recorded as weak ("Weak" in Table 1) when percentage binding was between 1%-10%. ND=not determined.

TABLE 2

Binding of Anti-PROKR Antibodies to HEK293 Cells Expressing Human, Mouse or Monkey PROKR1 or PROKR2 Measured by Flow Cytometry

| Antibody | Human PROKR1 | Human PROKR2 | Mouse PROKR1 | Mouse PROKR2 | Monkey PROKR1 | Monkey PROKR2 |
|---|---|---|---|---|---|---|
| H4H6663P | Pos | Pos | ND | ND | ND | ND |
| H4H6669P | Neg | Neg | ND | ND | ND | ND |
| H4H6671P | Neg | Neg | ND | ND | ND | ND |
| H4H6680P | Neg | Neg | ND | ND | ND | ND |
| H4H6690P | Pos | Neg | ND | ND | ND | ND |
| H4H6696P | Pos | Neg | ND | ND | ND | ND |
| H4H6698P | Pos | Pos | Pos | Pos | Pos | Pos |
| H4H6701P | Pos | Pos | Pos | Pos | Pos | Pos |

TABLE 2-continued

Binding of Anti-PROKR Antibodies to HEK293 Cells Expressing Human, Mouse or Monkey PROKR1 or PROKR2 Measured by Flow Cytometry

| Antibody | Human PROKR1 | Human PROKR2 | Mouse PROKR1 | Mouse PROKR2 | Monkey PROKR1 | Monkey PROKR2 |
|---|---|---|---|---|---|---|
| H4H6706P | Neg | Neg | ND | ND | ND | ND |
| H2M6385N | Weak | Pos | Neg | Pos | Neg | Pos |
| H1M6386N | Weak | Pos | Neg | Neg | Neg | Neg |

As shown in Table 2, five antibodies bound to cells expressing human PROKR1 and to cells expressing human PROKR2: H4H6663P, H4H6698P, H4H6701P, H2M6385N and H1M6386N (with H2M6385N and H1M6386N binding only weakly to cells expressing human PROKR1). Two of the antibodies tested bound to cells expressing human PROKR1 but not to cells expressing human PROKR2: H4H6690P and H4H6696P.

Antibodies H4H6698P and H4H6701P, which bound to cells expressing human PROKR1 and cell expressing human PROKR2, also exhibited positive binding to cells expressing mouse and monkey PROKR1 and PROKR2. Antibody H2M6385N, which bound only weakly to cells expressing human PROKR1, was negative for binding to mouse and monkey PROKR1 but was positive for binding to mouse and monkey PROKR2.

Thus, as illustrated by this example, the present invention includes: (a) antibodies that specifically bind human PROKR1 and human PROKR2; (b) antibodies that specifically bind human PROKR1 and human PROKR2, as well as PROKR1 and PROKR2 from non-human species (e.g., mouse and monkey); and (c) antibodies that specifically bind human PROKR1 but not human PROKR2. Anti-PROKR antibodies with binding specificity patterns, other than those specifically illustrated in this Example, are also contemplated within the scope of the present invention.

Example 4

Determination of the Equilibrium Binding Constants for Anti-PROKR Antibodies Binding to PROKR1 and PROKR2 by Surface Plasmon Resonance (Biacore)

Equilibrium dissociation constants ($K_D$ values) were determined for antigen binding to selected purified anti-PROKR antibodies generated in accordance with Example 1 by surface kinetics using a real-time surface plasmon resonance biosensor (Biacore 4000) assay at 25° C. For these experiments, antibody was captured on either a goat anti-mouse IgG polyclonal antibody (GE Healthcare, #BR-1008-38) or a mouse anti-human IgG (Fc) monoclonal antibody (GE Healthcare, #BR-1008-39) surface created through direct amine coupling to a Biacore CM5 sensor chip. Kinetic experiments were carried out using HBS-EP (10 mM HEPES, 150 mM NaCl, 3 mM EDTA, 0.05% Surfactant P20, pH 7.4) as both the running buffer and the sample buffer. Antigen-antibody association rates were measured by injecting 2 concentrations (25 and 100 nM) of both human PROKR1(1-62)-hFc (SEQ ID NO:179) and human PROKR2(1-53)-hFc (SEQ ID NO:180) over the captured antibody surface. Antibody-antigen association was monitored for 90 seconds while dissociation was monitored for 360 seconds. Kinetic on-rate ($k_a$) and off-rate ($k_d$) constants were determined from the data using Scrubber software version 2.0 c. Binding dissociation equilibrium constants ($K_D$) and dissociative half-lives ($t_{1/2}$) were calculated from the kinetic rate constants as: $K_D = k_d/k_a$ and $t_{1/2} = \ln(2)/k_d$. Results are shown in Tables 3 (PROKR1 binding) and 4 (PROKR2 binding) (NB=no binding observed).

TABLE 3

Binding Kinetics of Anti-PROKR Antibodies binding to Human PROKR1

| Antibody | $k_a$ (1/Ms) | $k_d$ (1/s) | $K_D$ (M) | $t_{1/2}$ (min) |
|---|---|---|---|---|
| H1M6386N | $2.12 \times 10^5$ | $1.03 \times 10^{-3}$ | $4.85 \times 10^{-9}$ | 11 |
| H4H6385N | $2.94 \times 10^5$ | $1.36 \times 10^{-4}$ | $4.61 \times 10^{-10}$ | 85 |
| H4H6663P | $5.83 \times 10^5$ | $6.20 \times 10^{-3}$ | $1.06 \times 10^{-8}$ | 2 |
| H4H6669P | $2.36 \times 10^5$ | $6.23 \times 10^{-5}$ | $2.64 \times 10^{-10}$ | 186 |
| H4H6671P | $1.98 \times 10^5$ | $3.62 \times 10^{-4}$ | $1.83 \times 10^{-9}$ | 32 |
| H4H6680P | $2.31 \times 10^5$ | $4.55 \times 10^{-5}$ | $1.97 \times 10^{-10}$ | 254 |
| H4H6690P | $5.45 \times 10^5$ | $1.59 \times 10^{-3}$ | $2.92 \times 10^{-9}$ | 7 |
| H4H6696P | $3.17 \times 10^5$ | $7.27 \times 10^{-4}$ | $2.30 \times 10^{-9}$ | 16 |
| H4H6698P | $2.55 \times 10^5$ | $2.87 \times 10^{-4}$ | $1.12 \times 10^{-9}$ | 40 |
| H4H6701P | $3.85 \times 10^5$ | $4.12 \times 10^{-4}$ | $1.07 \times 10^{-9}$ | 28 |
| H4H6706P | $1.96 \times 10^5$ | $2.13 \times 10^{-4}$ | $1.09 \times 10^{-9}$ | 54 |

TABLE 4

Binding Kinetics of Anti-PROKR Antibodies binding to Human PROKR2

| Antibody | $k_a$ (1/Ms) | $k_d$ (1/s) | $K_D$ (M) | $t_{1/2}$ (min) |
|---|---|---|---|---|
| H1M6386N | NB | NB | NB | NB |
| H4H6385N | $4.89 \times 10^5$ | $5.39 \times 10^{-3}$ | $1.10 \times 10^{-8}$ | 2 |
| H4H6663P | $1.04 \times 10^5$ | $1.34 \times 10^{-2}$ | $1.29 \times 10^{-7}$ | 1 |
| H4H6669P | NB | NB | NB | NB |
| H4H6671P | NB | NB | NB | NB |
| H4H6680P | $5.99 \times 10^4$ | $2.53 \times 10^{-4}$ | $4.23 \times 10^{-9}$ | 46 |
| H4H6690P | NB | NB | NB | NB |
| H4H6696P | $7.63 \times 10^5$ | $1.63 \times 10^{-2}$ | $2.14 \times 10^{-8}$ | 1 |
| H4H6698P | $5.33 \times 10^5$ | $8.57 \times 10^{-3}$ | $1.61 \times 10^{-8}$ | 1 |
| H4H6701P | $8.91 \times 10^5$ | $2.15 \times 10^{-3}$ | $2.41 \times 10^{-9}$ | 5 |
| H4H6706P | NB | NB | NB | NB |

As shown in Table 3, eleven anti-PROKR antibodies demonstrated binding to the human PROKR1(1-62)-hFc protein with $K_D$ values ranging from 197 pM to 10.6 nM. As shown in Table 4, six of the 11 anti-PROKR antibodies demonstrated binding to the human PROKR2(1-53)-hFc protein with $K_D$ values ranging from 2.41 nM to 129 nM. Five antibodies (H1M6386N, H4H6669P, H4H6671P, H4H6690P, and H4H6706P) did not demonstrate any measurable binding to the human PROKR2(1-53)-hFc protein in this assay format.

Example 5

Ability of Anti-PROKR Antibodies to Inhibit Prokineticin-Mediated Calcium Mobilization in Cells Engineered to Stably Express PROKR1 or PROKR2

The ability of anti-PROKR antibodies to block activation of PROKR1 and PROKR2 by their ligands prokineticin 1 (PK1) and prokineticin 2 (PK2) in vitro was determined using a cell-based assay as described below.

HEK293 cells were modified to stably express either human PROKR1 (293/hPROKR1), human PROKR2 (293/hPROKR2), mouse PROKR1 (293/mPROKR1), rat PROKR1 (293/rPROKR1), cynomolgus monkey PROKR1 (293/mfPROKR1) or cynomolgus monkey PROKR2 (293/mfPROKR2). For these experiments, the PROKR-expressing cell lines were maintained in complete growth medium [DME High Glucose (Irvine Scientific, #9033), 10% fetal bovine serum (Irvine Scientific, #3000A), 1% pencillin/streptomycin/glutamine (GIBCO, #10378), and 500 µg/ml G418 (GIBCO, #11811-098)].

Intracellular calcium levels were measured using a Fluo-4 NW Calcium Assay Kit (Invitrogen, #F36206). To assess the ability of anti-PROKR antibodies to inhibit human PK1-or human PK2-dependent calcium mobilization, cells expressing PROKR1 or PROKR2 were seeded in 96 well assay plates at 20,000-50,000 cells per well in complete growth medium and allowed to grow overnight at 37° C. in 5% $CO_2$. The next day the cell culture medium was replaced with Fluo-4 NW kit assay buffer plus calcium indicator dye as per manufacturer's specifications. For the inhibition curves, anti-human PROKR antibodies were added to the cells at final concentrations ranging from 17 pM to 1 µm and incubated for 1 hour (30 minute incubation at 37° C. followed by 30 minute incubation at room temperature). Human PK1 (Cell Sciences; #CRV015B) or hPK2 (ProSci Inc.; #40-190) were then added for each antibody dose response to achieve a constant ligand concentration (as shown in the corresponding tables). Relative fluorescence units (RFU) were measured every second for at least 50 seconds using FLIPR Tetra high throughput cellular screening system (Molecular Devices). For hPK1 and hPK2 dose-response curves, each ligand was added to cells without antibody at concentrations ranging from 70 pM to 500 nM, and then the RFU values were measured. The max—min RFU was calculated for each well and $EC_{50}/IC_{50}$ values were determined from a four-parameter logistic equation over an 8 or 12-point response curve (GraphPad Prism). Results are shown in Tables 5-8. For the experiments depicted in Table 8, 1 nM of hPK1 was the constant concentration used in both assays.

TABLE 5

$EC_{50}$ Values for hPK1 or hPK2 Stimulation of HEK293 Cells Expressing Human and Monkey PROKR1 and PROKR2 And Constant Ligand Concentrations Used for $IC_{50}$ Determinations

| | | $EC_{50}$ (nM)/Ligand Constant (nM) | | | |
|---|---|---|---|---|---|
| | | Human PROKR1 | Human PROKR2 | Monkey PROKR1 | Monkey PROKR2 |
| hPK1 ligand | Experiment 1 | 6.2/20 | ND | 69/20 | ND |
| | Experiment 2 | 14.3/20 | 8.7/10 | ND | ND |
| | Experiment 3 | 2.2/1 | 12.7/20 | 5/5 | 22.6/25 |
| hPK2 ligand | Experiment 1 | 30.7/20 | ND | ND | ND |
| | Experiment 2 | ND | 156/9 | ND | ND |
| | Experiment 3 | 0.6/1 | 3.7/5 | 0.1/0.5 | 0.3/0.5 |

TABLE 6

$IC_{50}$ Values for Anti-PROKR Antibody Inhibition of Calcium Flux in hPK1- or hPK2-Stimulated HEK293 Cells Expressing Human PROKR1 and Human PROKR2

| | hPROKR1 + PK1 | | hPROKR1 + PK2 | | hPROKR2 + PK1 | | hPROKR2 + PK2 | |
|---|---|---|---|---|---|---|---|---|
| Antibody | $IC_{50}$ (nM) | Block (%) | $IC_{50}$ (nM) | Block (%) | $IC_{50}$ (nM) | Block (%) | $IC_{50}$ (nM) | Block (%) |
| H1M6386N | 14.9* | 92.03* | 16.2* | 66.60* | ND | ND | ND | ND |
| H4H6663P | >1000** | 15.48** | ND | ND | NB** | 0** | NB** | 0** |
| H4H6669P | 14** | 52.42** | ND | ND | NB** | 0** | NB** | 0** |
| H4H6671P | 14.5** | 45.00** | ND | ND | NB** | 0** | NB** | 0** |
| H4H6680P | 16.4** | 51.05** | ND | ND | NB** | 0** | NB** | 0** |
| H4H6690P | >1000** | 24.70** | ND | ND | NB** | 0** | NB** | 0** |
| H4H6696P | 13.1*** | 101.04*** | >300*** | 32.85*** | NB*** | 0*** | NB*** | 0*** |
| H4H6698P | 8.5*** | 100.58*** | >300*** | 40.03*** | NB*** | 0*** | NB*** | 0*** |
| H4H6701P | 6.6*** | 98.55*** | >300*** | 56.62*** | >300*** | 48.56*** | >300*** | 60.80*** |
| H4H6706P | 11.2** | 59.12** | ND | ND | NB** | 0** | NB** | 0** |
| H4H6385N | 6.3*** | 100.89*** | 55.1*** | 77.52*** | NB*** | 0*** | NB*** | 0*** |

ND: not determined

NB: no blocking observed

*= Used constant ligand concentration shown for Experiment 1 in Table 5

**= Used constant ligand concentration shown for Experiment 2 in Table 5

***= Used constant ligand concentration shown for Experiment 3 in Table 5

TABLE 7

IC$_{50}$ Values for Anti-PROKR Antibody Inhibition of Calcium Flux in hPK1- or hPK2-Stimulated HEK293 Cells Expressing Monkey PROKR1 and Monkey PROKR2

| Antibody | MfPROKR1 + PK1 | | MfPROKR1 + PK2 | | MfPROKR2 + PK1 | | MfPROKR2 + PK2 | |
|---|---|---|---|---|---|---|---|---|
| | IC$_{50}$ (nM) | Block (%) | IC$_{50}$ (nM) | Block (%) | IC$_{50}$ (nM) | Block (%) | IC$_{50}$ (nM) | Block (%) |
| H1M6386N | NB* | 0* | ND | ND | ND | ND | ND | ND |
| H4H6696P | 31*** | 93.91*** | >300*** | 67.92*** | NB*** | 0*** | NB*** | 0*** |
| H4H6698P | 32.9*** | 99.34*** | 63.9*** | 85.74*** | NB*** | 0*** | NB*** | 0*** |
| H4H6701P | 6.4*** | 100.67*** | >300*** | 50.53*** | >300*** | 21.36*** | >300*** | 61.21*** |
| H4H6385N | 6.7*** | 100.82*** | 51.8*** | 93.70*** | NB*** | 0*** | NB*** | 0*** |

ND: not determined
NB: no blocking observed
*= Used constant ligand concentration shown for Experiment 1 in Table 5
***= Used constant ligand concentration shown for Experiment 3 in Table 5

TABLE 8

IC$_{50}$ Values for Anti-PROKR Antibody Inhibition of Calcium Flux in hPK1-Stimulated HEK293 Cells Expressing Mouse PROKR1 and Rat PROKR1

| | mPROKR1 + PK1 | | rPROKR1 + PK1 | |
|---|---|---|---|---|
| Antibody | IC$_{50}$ (nM)* | Block (%) | IC$_{50}$ (nM)** | Block (%) |
| H4H6669P | NB | 0 | ND | ND |
| H4H6671P | NB | 0 | ND | ND |
| H4H6680P | NB | 0 | ND | ND |
| H4H6696P | NB | 0 | NB | 0 |
| H4H6698P | NB | 0 | NB | 0 |
| H4H6701P | >300 | 20.85 | NB | 0 |
| H4H6385N | NB | 0 | NB | 0 |

ND: not determined
NB: no blocking observed
*= Observed hPK1 EC$_{50}$ value (no antibody) was 0.9 nM
**= Observed hPK1 EC$_{50}$ value (no antibody) was 0.7 nM Eleven anti-PROKR1 antibodies were tested for inhibition of hPK1-mediated calcium mobilization in 293/hPROKR1 cells. As shown Table 6, four antibodies (H4HM6385N, H4H6701P, H4H6698P, and H4H6696P) blocked >98% of the PROKR1 activity with IC$_{50}$ values ranging from 6.3 nM to 13.1 nM. Another anti-PROKR antibody, H1M6386N, blocked >92% of the hPK1 mediated calcium mobilization of 293/hPROKR1 cells with an IC$_{50}$ value of 14.9 nM. Four anti-PROKR antibodies (H4H6669P, H4H6671P, H4H6680P, H4H6706P) blocked between 45% to 60% of the hPK1-mediated calcium mobilization in 293/hPROKR1 cells with IC$_{50}$ values ranging from 11.2 nM to 16.4 nM. Two anti-PROKR antibodies (H4H6663P and H4H6690P) blocked less than 25% of the hPK1-mediated calcium mobilization in 293/hPROKR1 cells.

Five anti-PROKR antibodies were also tested for inhibition of hPK2-mediated calcium mobilization in 293/hPROKR1 cells as shown in Table 6. One anti-PROKR antibody, H4HM6385N, blocked >77% of the hPK2-mediated calcium mobilization in 293/hPROKR1 cells with an IC$_{50}$ value of 55.1 nM, while 2 anti-PROKR antibodies (H1M6386N and H 4H6701P) blocked approximately 67% to 57% of the calcium mobilization with IC$_{50}$ values of 16.2 nM and >300 nM. Two anti-PROKR antibodies (H4H6696P and H4H6698P) blocked approximately 40% and 33% of the hPK2-mediated calcium mobilization in 293/hPROKR1 cells with IC$_{50}$ values>300 nM.

Ten anti-PROKR antibodies were also tested for inhibition of human PROKR2 function, as shown in Table 6. H4H6701P blocked hPK1-or hPK2-mediated calcium mobilization of 293/hPROKR2 cells under these assay conditions. This antibody blocked approximately 49% of the hPK 1-mediated calcium mobilization and approximately 61% of the hPK2-mediated calcium mobilization with IC$_{50}$ values>300 nM for both. None of the other tested antibodies blocked hPK1-or hPK2-mediated calcium mobilization of 293/hPROKR2 cells.

Five of the anti-PROKR antibodies were further tested for their ability to inhibit hPK1-mediated calcium flux in cells expressing cynomolgus monkey PROKR1 as shown in Table 7. Four antibodies (H4H6385N, H4H6701P, H4H6696P, and H4H6698P) blocked >90% of the hPK1-mediated calcium mobilization in 293/MfPROKR1 cells with IC$_{50}$ values ranging from 6.4 nM to 32.9 nM. One antibody, H1M6386N, did not measurably block hPK1-mediated calcium mobilization in 293/MfPROKR 1 cells. Four of the anti-PROKR antibodies were also tested for their ability to inhibit hPK2-mediated calcium flux in cells expressing cynomolgus monkey PROKR1 as shown in Table 7. One anti-PROKR antibody, H4H6385N blocked approximately 94% of hPK2-mediated calcium mobilization in 293/MfPROKR1 cells with an IC$_{50}$ value of 51.8 nM. Another anti-PROKR antibody, H4H6698P, blocked approximated 86% of the hPK2-mediated calcium mobilization in 293/MfPROKR1 cells with an IC$_{50}$ value of 63.9 nM. The two other anti-PROKR antibodies tested (H4H6696P and H4H6701P) blocked approximately 68% and 51% of the hPK2-mediated calcium mobilization in 293/MfPROKR1 cells with an IC$_{50}$ values>300 nM. These four antibodies were also tested for their ability to inhibit hPK1-or hPK2-mediated calcium flux in cells expressing monkey PROKR2 as shown in Table 7. H4H6701P blocked approximately 21% of the hPK1-mediated calcium mobilization and blocked 61% of the hPK2-mediated calcium mobilization with IC$_{50}$ values>300 nM for both. The other three tested antibodies did not block hPK1-or hPK2-mediated calcium mobilization of 293/MfPROKR2 cells under these assay conditions.

Seven of the anti-PROKR antibodies were tested for their ability to block hPK1-mediated calcium flux in cells expressing mouse PROKR1 as shown in Table 8. H4H6701P blocked approximately 21% of the hPK1-mediated calcium mobilization of 293/mPROKR1 cells with an IC$_{50}$ value>300 nM, and the other 6 tested antibodies did not block in this assay. Four of the anti-PROKR antibodies were tested for their ability to block hPK1-mediated calcium flux in cells expressing rat PROKR1 as shown in Table 8. None of the tested anti-PROKR antibodies blocked stimulation of 293/rPROKR1 by hPK1 under these assay conditions.

Example 6

Ability of Anti-PROKR Antibodies to Inhibit Prokineticin-Mediated Calcium Mobilization in Cells Engineered For Inducible Expression of PROKR1 or PROKR2

The ability of anti-human PROKR antibodies to block activation of prokineticin receptor 1 (PROKR1) and prokineticin receptor 2 (PROKR2) by their ligands prokineticin 1 (PK1) and prokineticin 2 (PK2) in vitro was determined using a cell-based assay as described below.

CHO cells were modified for inducible expression of either human PROKR1 (CHO/hPROKR1), human PROKR2 (CHO/hPROKR2), mouse PROKR1 (CHO/mPROKR1), or mouse PROKR2 (CHO/mPROKR2). For these experiments, the PROKR-expressing cell lines were generated and maintained in complete growth medium [DME High Glucose (Irvine Scientific, #9033), 10% fetal bovine serum (Irvine Scientific, #3000A), 1% penicillin/streptomycin/glutamine (GIBCO, #10378), and 500 µg/mL G418 (GIBCO, #11811-098)]. To induce PROKR expression, CHO cell lines were grown in the presence of 0.5 mg/mL doxycycline for 16 to 24 hours. Non-induced cells were handled in an identical manner, but in the absence of doxycycline. As determined by FACS, PROKR surface staining was present on CHO cells even in the absence of the inducer, but at a lower level than in the presence of the inducer.

Intracellular calcium levels were measured using a Fluo-4 NW Calcium Assay Kit (Invitrogen, #F36206) as per the manufacturer's specifications. To assess the ability of anti-PROKR antibodies to inhibit human PK1-or human PK2-dependent calcium mobilization, CHO cell lines were grown in the presence or absence of doxycycline. Cells were then seeded in 96 well assay plates at 125,000 cells per well in Fluo-4 NM assay buffer, incubated for 1 hour at 37° C. in 5% $CO_2$, and an equivalent volume of Fluo-4 NW kit assay buffer plus calcium indicator dye was then added to each well. For the inhibition curves, anti-human PROKR antibodies were added to the cells at final concentrations ranging from 1.0 µM to 1.3 nM and incubated for 1 hour (30 minute incubation at 37° C. followed by 30 minute incubation at room temperature). Constant concentrations of hPK1 or hPK2 (as shown in the corresponding figures) were then added to cells that had been pre-incubated with antibody, and relative fluorescence units (RFU) were measured every second for at least 50 seconds using FLIPR Tetra (Molecular Devices). For hPK1 and hPK2 dose-response curves, each ligand was added to cells without antibody at concentrations ranging from 10 pM to 300 nM, and RFU were measured as for the antibody inhibition curves. The max—min RFU was calculated for each concentration and $EC_{50}/IC_{50}$ values were determined from a four-parameter logistic equation over an 8 or 12-point response curve (GraphPad Prism). Ligand $EC_{50}$ values or mean $EC_{50}$ values (±SEM) are shown in Table 9.

TABLE 9

Ligand $EC_{50}$ Values on Non-induced and Induced CHO/hPROKR1, CHO/hPROKR2, CHO/mPROKR1, and CHO/mPROKR2 Cell Lines

| | Ligand $EC_{50}$ (nM) | |
|---|---|---|
| Cell line | hPK1 | hPK2 |
| CHO/hPROKR1 (non-induced) | 48 (±14.3) | 1.4 (±0.58) |
| CHO/hPROKR1 (induced) | 2.0 (±0.82) | 1.6 (±0.96) |
| CHO/hPROKR2 (induced) | 40 (±34.95) | 9.8 (±9.4) |
| CHO/mPROKR1 (non-induced) | 8.3 | 0.8 |
| CHO/mPROKR1 (induced) | 1.5 | 9.6 |
| CHO/mPROKR2 (non-induced) | 112 | 18 |
| CHO/mPROKR2 (induced) | 4.5 | 2.2 |

Four anti-PROKR 1 antibodies were tested for inhibition of hPK1 and hPK2-mediated calcium mobilization in non-induced or induced CHO/hPROKR1, CHO/hPROKR2, CHO/mPROKR1, and CHO/mPROKR2 cell lines. Blocking results in the non-induced CHO/hPROKR1 cell line are shown in Table 10.

TABLE 10

Blocking of hPK1 and hPK2 Induced Calcium Flux on Non-Induced CHO/hPROKR1 Cell Line

| | CHO/hPROKR1 non-induced $IC_{50}$ (nM) | |
|---|---|---|
| Antibody | PK1 | PK2 |
| H4H6385N | 14.2 (±9.43)* | 20.0 (±10.4)*** |
| H4H6701P | 4.1** | 21.9*** |
| H4H6696P | 3.8** | 19.1*** |
| H4H6698P | 3.1** | 27.4*** |

*$IC_{50}$ values for H4H6385N are an average of experiments that used either 40 nM or 80 nM constant concentration of hPK1
**Experiment used 40 nM constant concentration of hPK1
***Experiment used 4 nM constant concentration of hPK2

As shown in Table 10, all four antibodies tested (H4HM6385N, H4H6701P, H4H6696P, and H4H6698P) blocked hPK1 mediated calcium flux in the non-induced CHO/hPROKR1 cell line (low hPROKR1 expressing cells) to near baseline levels with $IC_{50}$ values ranging from 3.1 nM to 14.2 nM. These same antibodies also blocked hPK2-mediated calcium flux in the non-induced CHO/hPROKR1 cell line to near baseline line levels with $IC_{50}$ values ranging from 19.1 nM to 27.4 nM. No blocking was observed in the induced CHO/hPROKR1 cell line (high expressing hPROKR1 cells) following ligand activation with either PK1 or PK2. None of the antibodies tested demonstrated blockade of hPK1 or hPK2-mediated calcium flux in the induced CHO/hPROKR2 cell line. Ligand activation of non-induced CHO/hPROKR2 cells was weak and inconsistent (data not shown), so antibody blockade could not be evaluated. None of the anti-PROKR antibodies tested blocked stimulation of non-induced or induced CHO/mPROKR1 and CHO/mPROKR2 cell lines with hPK1 or hPK2 under identical assay conditions.

The results of this Example confirm that anti-PROKR antibodies H4H6385N, H4H6701P, H4H6696P and H4H6698P effectively block PK1-and PK2-mediated PROKR1 signaling.

Example 7

Efficacy of an Anti-PROKR Antibody in a Model of DSS-Induced Colitis

In this Example, the ability of the anti-PROKR antibody H4H6385N to attenuate changes in open field behaviors following 7 days of oral dextran sodium sulfate administration (DSS, 4% w/v in drinking water) or water control was assessed.

Humanized Prokr1 mice, in which the coding sequence of the mouse Prokr1 gene was replaced with the corresponding human PROKR1 sequence, were used in this experiment (mixed male and female, 21-31 weeks of age). Separate cohorts of mice received 30 mg/kg (s.c.) of an isotype control antibody, 30 mg/kg (s.c.) of H4H6385N, or no injection. DSS administration was initiated 24 hours after antibody dosing. All mice were then tested in an automated open field apparatus (Kinder Scientific SmartFrame, Poway, Calif.).

Figure 1B:
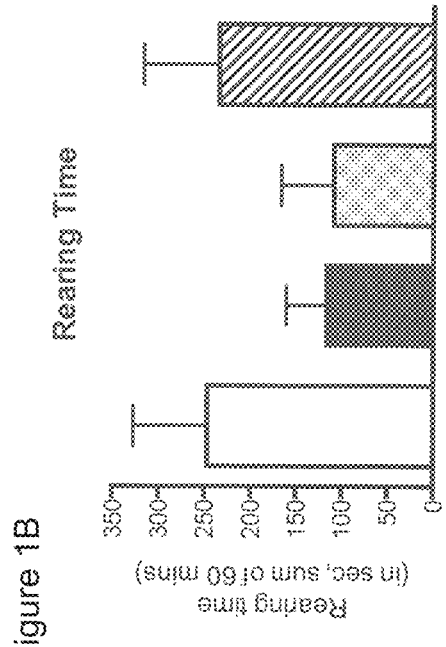
FIG. 1B depicts the total distance traveled in cm.
Figure 1C:
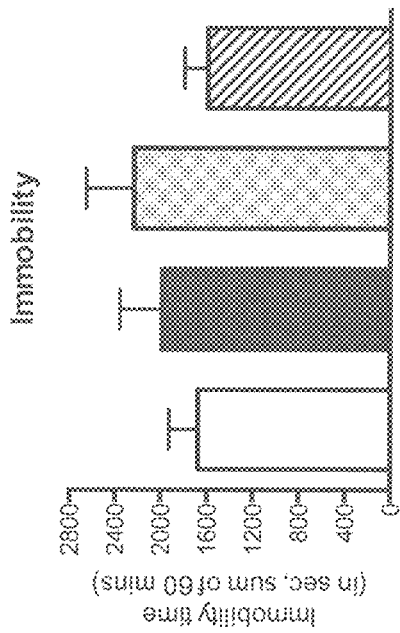
FIG. 1C depicts the rearing counts.
Figure 1D:
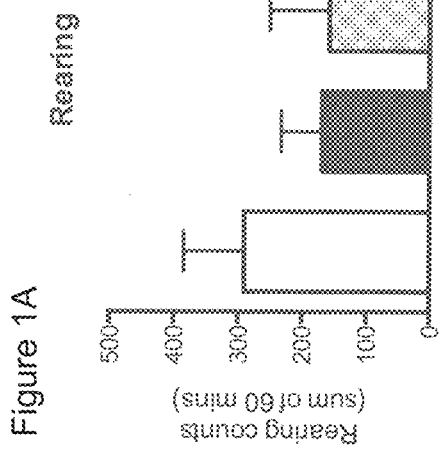
FIG. 1D depicts the rearing time in seconds. All parameters were measured over a 60 minute test period. The study summarizes open field behaviors of mice subjected to a DSS-induced colitis model. Mice were treated with either: water alone, DSS alone, DSS+ isotype control antibody, or DSS+antibody H4H6385N, as indicated.

It has been previously observed that DSS-induced colitis reliably alters 4 parameters of the open field assay: time spent immobile (immobility), the total amount of exploratory activity (total distance), the number of times that the mouse rears onto its hind limbs (rearing) and the amount of time it spends rearing onto its hind limbs (rearing time). The results of this experiment, expressed as the sum of the total time spent performing each behavior or the total counts of each behavior (as appropriate) of over the test period of 60 minutes, are shown in FIGS. 1A-1D (all data are represented as group mean±SEM. Each cohort is n=8-9/group).

As summarized in FIGS. 1A-1D, mice treated with the exemplary anti-PROKR antibody H4H6385N prior to DSS administration exhibited improved open field behaviors (i.e., reduced immobility, increased total distance, and increased rearing) as compared to untreated and isotype control-treated mice subjected to equivalent DSS administration conditions.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

---

What is claimed is:

1. An isolated antibody or antigen-binding fragment thereof that specifically binds cell surface-expressed prokineticin receptor 1 (PROKR1) and cell surface-expressed prokineticin receptor 2 (PROKR2) and blocks prokineticin-mediated activation of the PROKR1, wherein the antibody or antigen-binding fragment comprises three heavy chain complementarity determining regions (CDRs) of a heavy chain variable region comprising the amino acid sequence set forth in SEQ ID NO: 18; and three light chain CDRs of a light chain variable region comprising the amino acid sequence set forth in SEQ ID NO:26.

2. The antibody or antigen-binding fragment of claim 1, wherein the antibody or antigen-binding fragment thereof blocks prokineticin-1 (PK1)-mediated activation of PROKR1.

3. The antibody or antigen-binding fragment of claim 1, wherein the antibody or antigen-binding fragment thereof blocks prokineticin-2 (PK2)-mediated activation of PROKR1.

4. The antibody or antigen-binding fragment of claim 1, wherein the antibody or antigen-binding fragment thereof blocks prokineticin-1 (PK1)-mediated activation of PROKR1 and prokineticin-2 (PK2)-mediated activation of PROKR1.

5. The antibody or antigen-binding fragment of claim 2, wherein the antibody or antigen-binding fragment thereof blocks PK1-mediated activation of PROKR1 with an $IC_{50}$ of less than 20 nM, as measured in a calcium mobilization assay using PROKR1-expressing cells stimulated with 1 to 20 nM PK1 in vitro.

6. The antibody or antigen-binding fragment of claim 5, wherein the antibody or antigen-binding fragment thereof blocks PK1-mediated activation of PROKR1 with an $IC_{50}$ of less than 10 nM, as measured in a calcium mobilization assay using PROKR1-expressing cells stimulated with 1 to 20 nM PK1 in vitro.

7. The antibody or antigen-binding fragment of claim 3, wherein the antibody or antigen-binding fragment thereof blocks PK2-mediated activation of PROKR1 with an $IC_{50}$ of less than 60 nM, as measured in a calcium mobilization assay using PROKR1-expressing cells stimulated with 1 to 20 nM PK2 in vitro.

8. The antibody or antigen-binding fragment of claim 7, wherein the antibody or antigen-binding fragment thereof blocks PK2-mediated activation of PROKR1 with an $IC_{50}$ of less than 20 nM, as measured in a calcium mobilization assay using PROKR1-expressing cells stimulated with 1 to 20 nM PK2 in vitro.

9. The isolated antibody or antigen-binding fragment of claim 1, wherein the antibody or antigen-binding fragment comprises:

HCDR1 comprising the amino acid sequence set forth in SEQ ID NO: 20;
HCDR2 comprising the amino acid sequence set forth in SEQ ID NO: 22;
HCDR3 comprising the amino acid sequence set forth in SEQ ID NO: 24;
LCDR1 comprising the amino acid sequence set forth in SEQ ID NO: 28;
LCDR2 comprising the amino acid sequence set forth in SEQ ID NO: 30; and
LCDR3 comprising the amino acid sequence set forth in SEQ ID NO: 32.

10. The antibody or antigen-binding fragment of claim 9, wherein the antibody or antigen-binding fragment comprises: (a) a heavy chain variable region (HCVR) comprising the amino acid sequence set forth in SEQ ID NO: 18; and (b) a light chain variable region (LCVR) comprising the amino acid sequence set forth in SEQ ID NO: 26.

11. A pharmaceutical composition comprising the antibody or antigen-binding fragment of claim 1, and a pharmaceutically acceptable carrier or diluent.

12. A composition comprising the antibody or antigen-binding fragment of claim 1 and one or more additional therapeutic agents.

13. The composition of claim 12, wherein the additional therapeutic agent is selected from the group consisting of an antiviral, an antibiotic, an analgesic, a corticosteroid, an opioid, and an NSAID (non-steroidal anti-inflammatory drug).

14. The composition of claim 12, wherein the additional therapeutic agent is selected from the group consisting of: an anti-NGF antibody, an anti-PAR2antibody, an anti-ASIC1 antibody, an anti-ASIC2 antibody, an anti-ASIC3 antibody, an anti-ASIC4 antibody, an anti-GFR alpha antibody, an anti-EGFR antibody, an anti-ErbB2 antibody, anti-ErbB3 antibody, an anti-ErbB4 antibody, an anti-EGFRvIII antibody, an anti-cMET antibody, an anti-IGF1R antibody, an anti-PDGFR-alpha antibody, an anti-PDGFR-beta antibody, a VEGF-Trap, an anti-VEGF antibody, an anti-DLL4 antibody, an anti-Ang2 antibody, an anti-FOLH1 antibody, an anti-PRLR antibody, an anti-STEAP1 antibody, an anti-STEAP2 antibody, an anti-TMPRSS2 antibody, an anti-MSLN antibody, an anti-CA9 antibody, an anti-uroplakin antibody, an anti-CD20 antibody, an anti-IL-1 antibody, an anti-IL-2 antibody, an anti-IL-3 antibody, an anti-IL-4 antibody, an anti-IL-5 antibody, an anti-IL-6 antibody, an anti-IL-8 antibody, an anti-IL-9 antibody, an anti-IL-11 antibody, an anti-IL-12 antibody, an anti-IL-13 antibody, an anti-IL-17 antibody, an anti-IL-18 antibody, an anti-IgE antibody, and an anti-TNF antibody.

* * * * *